(12) United States Patent
Numata et al.

(10) Patent No.: US 6,171,844 B1
(45) Date of Patent: Jan. 9, 2001

(54) MICROORGANISM AND METHOD FOR ENVIRONMENTAL PURIFICATION USING THE SAME

(75) Inventors: Koichi Numata, Nagoya; Yasushi Oda, Aichi-gun; Masami Miyata, Toyota; Yukio Okamura, Toyota; Toshiaki Kimura, Toyota; Masatoshi Uchida, Tsu; Osamu Asami, Konan, all of (JP)

(73) Assignee: Toyota Jidosha Kabushiki Kaisha, Toyota (JP)

( * ) Notice: Under 35 U.S.C. 154(b), the term of this patent shall be extended for 0 days.

(21) Appl. No.: 09/252,806

(22) Filed: Feb. 19, 1999

Related U.S. Application Data

(63) Continuation-in-part of application No. 09/065,018, filed on Apr. 17, 1998.

(30) Foreign Application Priority Data

Aug. 19, 1996 (JP) .................................................. 8-217456
Apr. 25, 1997 (JP) .................................................. 9-109553

(51) Int. Cl.⁷ .................................. C12N 1/20; B09B 3/00
(52) U.S. Cl. ...................................... 435/252.1; 435/262.5
(58) Field of Search ................................. 435/252.1, 262.5

(56) References Cited

U.S. PATENT DOCUMENTS

| | | |
|---|---|---|
| 4,664,805 | 5/1987 | Focht . |
| 4,959,315 | 9/1990 | Nelson et al. . |
| 5,071,755 | 12/1991 | Nelson et al. . |

FOREIGN PATENT DOCUMENTS

| | | |
|---|---|---|
| 196 47 847 | 5/1997 | (DE) . |
| 0 523 769 | 1/1993 | (EP) . |
| 62-84780 | 4/1987 | (JP) . |
| 64-34499 | 2/1989 | (JP) . |
| 2-92274 | 4/1990 | (JP) . |
| 2-503866 | 11/1990 | (JP) . |
| 3-292970 | 12/1991 | (JP) . |
| 4-501667 | 3/1992 | (JP) . |
| 4-502277 | 4/1992 | (JP) . |
| 5-502593 | 5/1993 | (JP) . |
| 5-212371 | 8/1993 | (JP) . |
| 6-70753 | 3/1994 | (JP) . |
| 6-296711 | 10/1994 | (JP) . |
| 7-123976 | 5/1995 | (JP) . |
| 8-66182 | 3/1996 | (JP) . |
| WO 89/09827 | 10/1989 | (WO) . |
| WO 90/05708 | 5/1990 | (WO) . |
| WO 90/06901 | 6/1990 | (WO) . |
| WO 92/06208 | 4/1992 | (WO) . |

OTHER PUBLICATIONS

J.J. Perry et al., *Chemical Abstracts*, 124:9 (1996), p. 445.
D.W. Wilcox et al., *Chemical Abstracts*, 122:22 (1995), p. 533.
L.A. Vandenberg et al., *Chemical Abstracts*, 122:21 (1995), p. 614.
G. Singh, *Chemical Abstracts*, 91:11 (1979), p. 405.

*Primary Examiner*—Herbert J. Lilling
(74) *Attorney, Agent, or Firm*—Kenyon & Kenyon

(57) ABSTRACT

A novel microorganism which has the following characteristics: morphology (coccoid, rod shaped), gram staining (+), spore forming (−), motility (−), relationship to oxygen (aerobic), oxidase test (−), catalase test (+), resistance to acid (−), rod-coccus cycle (+), and GC content of DNA (mole %) (73 (by HPLC)), and which can decompose chloroethylene. The microorganism can decompose in 24 hours 30 ppm of trichloroethylene, and decompose of 100 ppm of trichloroethylene by 50%.

39 Claims, 23 Drawing Sheets

Fig. 16

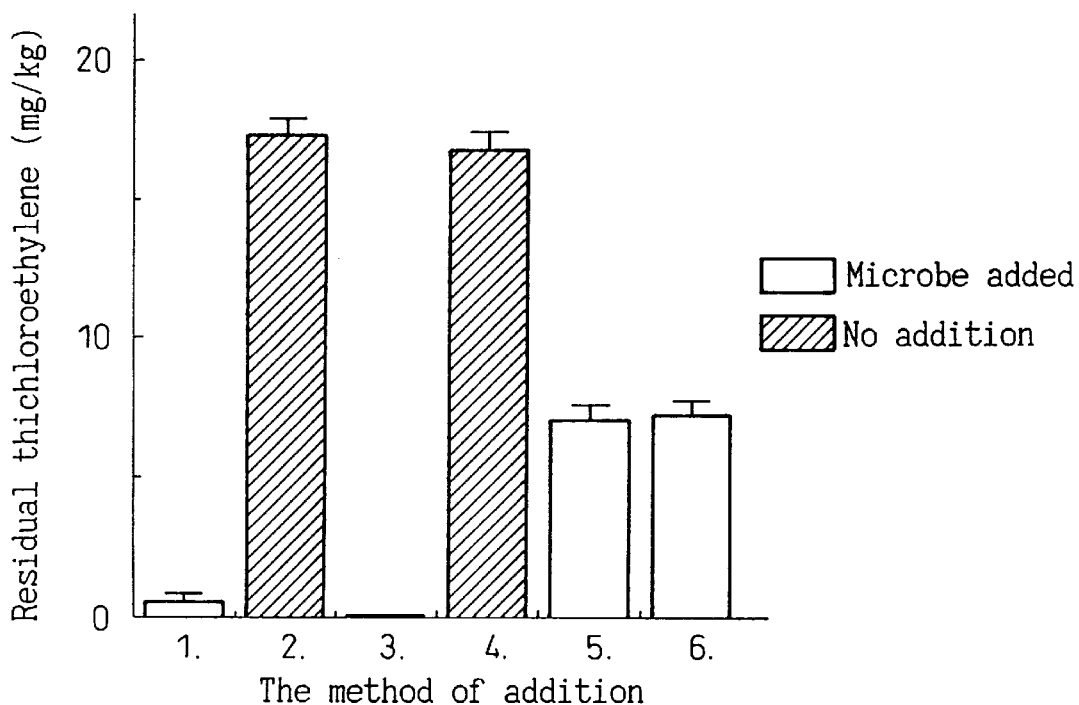

1. The MO7 culture liquid (15ml) suspended in the NMS medium was added at one addition.
2. Not added.
3. The MO7 culture liquid (7.5ml) suspended in the NMS medium was added twice.
(Total volume added is 15ml)
4. Not added.
5. The MO7 culture liquid (7.5ml) suspended in the NMS medium was added.
6. The MO7 culture liquid (7.5ml) suspended in the NMS medium was added at one addition (the final water content was adjusted to be 25%).

Fig.19

1. Test procedure

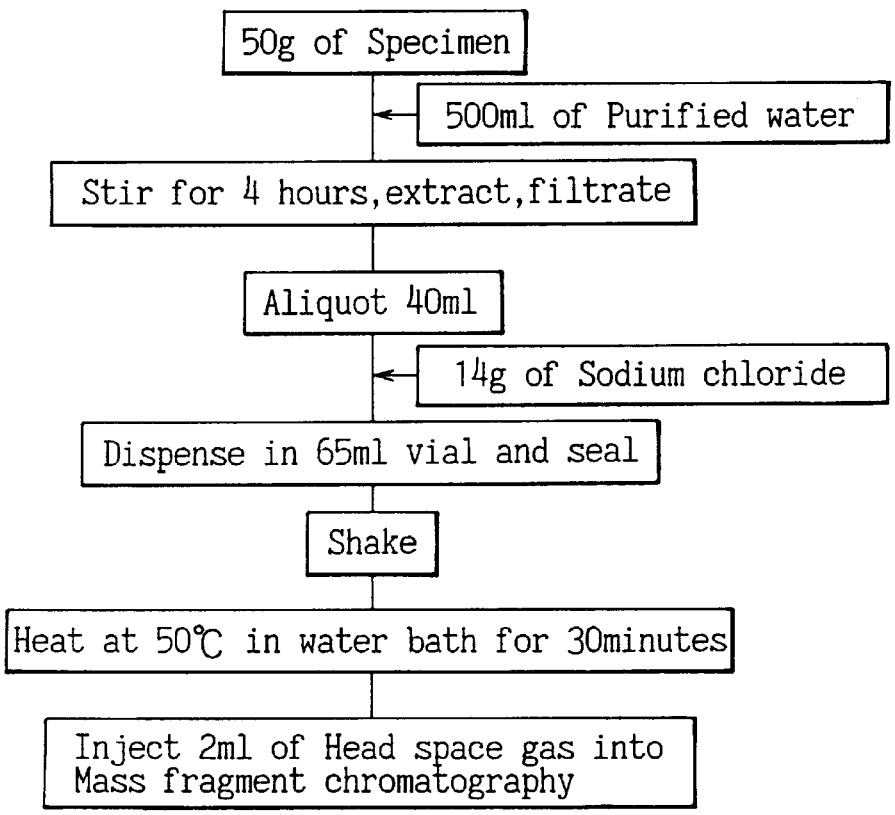

2. Operating conditions for gas chromatograph-mass spectrometer
Instrument: Shimazu Corp. GC-MS QP-1100EX
Column: 25% Silicone DC-550/Chromosorb WHP 80 to 100 mesh
glass tube, φ3mm×2.6m
Temperature: Injection port 250°C,
column 60°C (retain 1min) →
150°C (10°C/min temperature increase)
Gas flow rate: Helium 40ml/min
Temperature of ionization source: 250°C
Separator temperature: 250°C
Ionization potential: 70eV
Ionization method: EI
Preset Mass number: 62,64 (vinyl chloride)
96,98 (1,1-dichloroethylene,
cis-1,2-dichloroetylene and
trans-1,2-dichloroetylene)

1. Test procedure

2. Operating conditions for gaschromatography
Instrument: Shimazu GC-14A
Detector: ECD
Column: VOCOL, φ0.53mm×30m
Temperature: Injection port 200°C, detector 230°C
  column 50°C (retain 1min) →
  130°C (3°C/min temperature increase)
Gas pressure: Carrier gas (helium) 0.5kg/cm$^2$
Makeup gas (nitrogen): 0.9kg/cm$^2$ 1. Test procedure 2. Operating conditions for gaschromatography
Instrument: Shimazu GC-14A
Detector: ECD
Column: VOCOL, ϕ0.53mm×30m
Temperature: Injection port 200°C, detector 230°C
              column 40°C (retain 6min) →
              85°C (3°C/min temperature increase)
Gas pressure: Carrier gas (helium) 0.5kg/cm$^2$
Makeup gas (nitrogen): 0.9kg/cm$^2$ 1. Test procedure 2. Operating conditions for gas chromatograph-mass spectrometer
Instrument: Shimazu Corp. GC-MS QP-1100EX
Column: DB-1, ϕ0.53mm×30m
Temperature: Injection port 250°C, column 50°C
Gas flow rate: Helium 20ml/min
Temperature of ionization source: 250°C
Separator temperature: 250°C
Ionization potential: 70eV
Ionization method: EI
Mass number: 82

MICROORGANISM AND METHOD FOR ENVIRONMENTAL PURIFICATION USING THE SAME

CROSS REFERENCE

The present application is a continuation-in-part application of the patent application Ser. No. 09/065,018, filed on Apr. 17, 1998, the entire contents of which is incorporated herein by reference.

FIELD OF INVENTION

The present invention relates to new microorganisms which efficiently decompose organic halogenated compounds such as trichloroethylene, and to a method for decomposing organic halogenated compounds, specifically trichloroethylene in the soil, the underground water, or waste waters.

BACKGROUND OF INVENTION

In recent years, industrial utilization of organic solvents has been producing environmental polution problems by discharge of these compounds or waste waters containing these compounds in many parts of the nation. In particular, soil polution by organic chlorinated compounds is a major social problem, and the technology of repairing the contaminated soil has become more essential. The purification method of the contaminated soil includes physical methods and biological methods.

The physical treatment methods include the air-stripping method (a method of purging air into the contaminated soil which was excavated in order to volatize organic chlorinated compounds contained therein, and of removing them by adsorption on activated charcoal), and vacuum extraction methods (a method in which pipes are driven into the contaminated soil to create the state of reduced pressure so that the organic chlorinated compounds therein are volatized and extracted from the soil). However, these methods require an enormous power for purging the air etc., and have the drawbacks that the former methods require excavation of the soil, while in the latter the extraction efficiency is low and purification does not proceed smoothly under the low concentration of the contaminats. Furthermore, both methods only absorb the contaminating substances to the activated charcoal and therefore require a separate means to detoxicate the contaminating substances.

It has been reported recently that the biological treatment method which is under development utilizes the ability of microorganisms to decompose substances and can completely decompose or detoxicate the contaminating substances, and besides less energy is needed for the treatment as compared with the physical means. Moreover, the biological means permits purification even at low concentrations of contaminants and accordingly expectations on the method are great as a low-cost method for soil purification. The known biological methods include the solid-phase treatment (the excavated soil is mixed with phosphorus, nitrogen, microorganisms etc. to promote decomposition of the contaminating substances by the microorganisms), the slurry treatment method (the excavated soil is mixed with water, phosphorus, nitrogen, microorganisms etc. to treat in the liquid form to promote purification speed of the contaminating substances by the microorganisms), and the on-site treatment method (methane, the air, phosphorus, and nitrogen are injected into the soil without excavating the soil to promote decomposition of the contaminating substances by the microorganisms).

Of the conventionally used biological treatment methods, the solid-phase treatment method and the slurry treatment method require excavation of the soil and besides have a narrow range of application, and the cost for treatment and equipment is relatively high.

On the other hand, the on-site treatment method in which indegenous microorganisms are performed as degraders is less expensive in treatment and equipment compared with the methods described above, and can be applied on a wider range. But, under the condition that the absolute number of microorganisms in the soil is small, the purification rate of the on-site treatment decreases. Especially in the case of the compounds refractory to decomposition such as organic chlorinated compounds, purification is impossible when there are no living microorganisms which can decompose said contaminants in the soil. In such cases, it is believed that inoculation of the microorganisms having the ability of decomposing organic chlorinated compounds into the soil is essential for enhancement of the purification late of soil.

Known microorganisms which decompose trichloroethylene include *Methylosinus tricosporium* OB3 (Japanese Unexamined Patent Publication (Kohyo) No. 4(1992)-501667, Japanese Unexamined Patent Publication No. 5(1993)-212371), and *Methylosinus tricosporium* TUKUBA (Japanese Unexamined Patent Publication No. 2(1990)-92274, Japanese Unexamined Patent Publication No. 3(1991)-292970) which are methane-degradatating organisms, *Pseudomonas putida* F1 (Japanese Unexamined Patent Publication No. 64(1989)-34499), *Pseudomonas putida* BH (Fujita et al.; Chemical Engineering, 39(6):494–498, 1994), *Pseudomonas putida* UC-R5, UC-P2 (Japanese Unexamined Patent Publication No. 62(1987)-84780), *Pseudomonas putida* KWI-9 (Japanese Unexamined Patent Publication No. 6(1994)-70753), *Pseudomonas mendocina* KR1 (Japanese Unexamined Patent Publication No. 2(1990)-503866, 5(1993)-502593), *Pseudomonas cepacia* G4 (Japanese Unexamined Patent Publication No. 4(1992)-502277), and *Pseudomonas cepacia* KK01 (Japanese Unexamined Patent Publication No. 6(1994)-296711) which belong to the genus Pseudomonas, *Alcaligenes eutropus* JMP134 (A. R. Harker, Appl. Environ. Microbiol., 56(4):1179–1181, 1990), *Alcaligenes eutropus* KS01 (Japanese Unexamined Patent Publication No. 7(1995)-123976), *Nitrosomonas europaea* (D. Arciero et al., Biochem. Biophys. Res. Commun., 159(2):640–643, 1989) which is an ammonia-oxidizing bacterium, *Corynebacterium* J1 (Japanese Unexamined Patent Publication No. 8(1996)-66182) and the like.

The trichloroethylene-decomposing ability of these known microorganisms is not very high and most of these microorganisms can decompose 5 ppm of trichloroethylene in the liquid culture only. Furthermore, since decomposing ability of trichloroethylene in a special environment as the soil is required, it is necessary that the microorganism to be used for bioremediation not only has a sufficient ability of decomposing trichloroethylene but also can remain decomposing ability of trichloroethylene even in the soil. However, most of the known microorganisms are insufficient in this respect.

It is reported that *Pseudomonas cepacia* KK01 can decompose trichloroethylene at an initial concentration of 30 ppm to 15 ppm in the liquid culture, and trichloroethylene at an initial concentration of 5 ppm to 1 ppm in the soil (Japanese Unexamined Patent Publication No.-6(1994)-296711). Furthermore, it is reported that *Alcaligenes eutropus* KS01 can decompose trichloroethylene at an initial concentration of 50 ppm to below the level of detection in the liquid culture, and trichloroethylene at an initial concentration of 1 ppm to below the level of detection limit in the soil (Japanese Unexamined Patent Publication No. 7(1995)-123976).

It has been confirmed that these microorganisms have a higher decomposing ability than the conventional microorganisms and that these abilities can be exhibited even in the soil. However, addition of at least one or more than one aromatic compound is needed to the soil environment for induction of the decomposing abilities of these microorganisms. But, the aromatic compounds themselves are contaminants and therefore have a risk of causing a secondary pollution. It is a great challenge to be solved for practical application, therefore, to obtain a microorganism which enables an aromatic compound, when added, to be completely decomposed and removed together with trichloroethylene, or which permits decomposition of trichloroethylene without addition of an aromatic compound.

Accordingly, in order to put the biological purification of trichloroethylene into practical use, it has been desired to obtain a microorganism which has a high decomposing ability, and which enables an aromatic compound, when added, to be completely decomposed and removed together with trichloroethylene, or which permits decomposition of trichloroethylene without addition of an aromatic compound.

Furthermore, in many cases it is extremely difficult to increase the density of a microorganism to the level commensurate with its desired treatment capacity, because the density of the dispersed microorganism is suppressed low in the soil because of predation thereof by protozoa and competitive effects by autochthonous microorganism. In order to increase the density methods are employed such as the method of pressure pumping the air and nutrients into the soil. But despite the enormous energy required, it is difficult to increase the bacterial density by those means alone, thereby keeping the decomposing ability of microorganisms at low levels. Tremendous amounts of energy such as supply of nutrients, aeration etc. are needed to retain a high bacterial density in the closed system such as the reactor as well as in the open system.

If decomposition capability per unit amount of a bacterial mass is increased, a sufficient decomposition capability may be obtained even at low densities of the bacterial mass, thus obviating the need to put in a tremendous amount of energy for keeping the density of the bacterial mass. Though microorganisms which decompose trichloroethylene do so by expressing the enzyme capable of decomposing such substances, such expression of the enzyme requires an inducer. It has already been known that microorganisms can be allowed to exhibit their decomposition ability by adding an inducer and bringing the microorganisms into contact said inducer during culturing, but no previous studies have focused on the length of time of the contact and thereby on the methods to enhance the decomposition ability per unit amount of bacterial mass.

Bio-augmentation which comprises spreading trichloroethylene-decomposing microorganisms into the soil to effect decomposition of trichloroethylene etc. is currently hard to get social acceptance, since it has a potential risk of producing far-reaching effects on the ecological system by releasing a specific microorganism into the environment. But the spraying of a microorganism which has completely lost the propagating activity by sterilization treatment is equivalent to that of mere organic materials, and thus is believed to have little effect on the ecological system. The invention which was disclosed in Japanese post-examined Patent Publication No. 8(1996)-3012 claims that undesirable effects on the ecological system can be minimized by crushing the decomposing bacteria and then spraying them to the soil. But, it will be readily appreciated that the crushing procedure of microorganisms takes extensive equipment, a lot of time and labor, and thus the spraying of a large amount of decomposing bacterium to the contaminated soil will be in fact very difficult.

The above invention further lists the advantageous effects by slaiming that the crushed bacteria are easier to penetrate into the soil than the intact bacterial mass, but said invention makes no mention of duration of the decomposing ability retained by the crushed bacteria. Moreover, the known trichloroethylene-oxidase requires NAD as a coenzyme. But it would be extremely difficult to supply the coenzyme in the concentration necessary for the decomposition reaction of the enzyme which is released from the bacterial mass by crushing the bacterium because the coenzyme is very expensive.

DISCLOSURE OF THE INVENTION

Thus, it is an object of the present invention to provide new microorganisms which can decompose organic halogenated compounds such as trichloroethylene in a more efficient manner than the conventionally known microorganisms, and a method for decomposing organic halogenated compounds utilizing said microorganism. It is another object of the present invention to provide an inexpensive method for minimizing the effects on the ecological system after a specific microorganism has been released to the environment.

After intensive studies to solve the above-mentioned problems the inventors have successfully isolated a new microorganism which does not belong to any of the known genera of microorganisms and which has a very high ability of decomposing trichloroethylene as compared with any of the conventionally known microorganisms, and thereby completed the present invention.

Thus, the present invention provides a bacterium which has the following taxonomical properties:

TABLE 1

| | |
|---|---|
| Morphology | Coccoid, rod shaped |
| Gram staining | + |
| Spore forming | − |
| Motility | − |
| Relationship to oxygen | aerobic |
| Oxidase test | − |
| Catalase test | + |
| Resistance to acid | − |
| Rod-coccus cycle | + |
| Aerial mycelium forming | − |
| Peptide glycan type of cell wall | meso-diaminopimelic acid |
| Glycolyl test | − (acetyl type) |
| Mycolic acid | − |
| Major isoprenoid quinones | MK-8 (H4) |
| GC content of DNA (mole %) | 73 (by HPLC) | and, which can decompose trichloroethylene. A representative strain of the bacterium is strain MO7 (FERM BP-5624).

The present invention further provides a method for decomposing organic halogenated compounds and/or aromatic compounds, said method comprising allowing said bacterium to act on said organic halogenated compounds and/or aromatic compounds. In this case, an organic halogenated compound is importantly trichloroethylene, and an aromatic compound is preferably phenol.

The present invention further provides a method for decomposing organic halogenated compounds in the soil, waste waters, or other waste products containing organic halogenated compounds, said method comprising adding a culture of said bacterium to said soil, waste waters, or other waste products. An organic halogenated compound whicis important in terms of practical application thereof is trichloroethylene.

The bacterial culture as used herein is preferably a cultured bacterial mass. The cultured bacterial mass may be a living bacterial mass or a sterilized bacterial mass.

The present invention also provides a method for decomposing organic halogenated compounds in the soil, waste waters, or other waste products containing organic halogenated compounds, said method comprising inoculating the bacterium of the present invention to said soil, waste waters, or other waste products, adding an aromatic compound or a degradable carbon source or a mixture thereof to said soil, waste waters, or other waste products, and then culturing said inoculated microorganism. Said aromatic compound as used herein is preferably a phenolic compound, for example phenol, and said degradable carbon source as used herein is preferably a saccharide, for example glucose.

The present invention also provides a method for decomposing organic halogenated compounds aid/or aromatic compounds, in which a sterilized cultured bacterial mass of a microorganism which is capable of decomposing organic halogenated compounds and/or aromatic compounds is allowed to act on said organic halogenated compounds and/or said aromatic compounds. The present invention also provides a method for decomposing organic halogenated compounds and/or aromatic compounds in the soil, waste waters, or other waste products containing organic halogenated compounds and/or aromatic compounds, in which a sterilized cultured bacterial mass of a microorganism capable of decomposing said organic halogenated compounds and/or said aromatic compounds is added to said soil, waste waters, or other waste products. In the method described above, said sterilization treatment is, for example, ultraviolet irradiation.

The present invention also provides a decomposition agent of organic halogenated compounds and/or aromatic compounds, said agent comprising said cultured bacterial cells of the bacterium of the present invention. Said cultured bacterial mass may be a living bacterial mass or a sterilized bacterial mass. The sterilization treatment of them is, for example, ultraviolet irradiation. The bacterial mass contained in said decomposition agent is preferably in the form of a dried or freezed bacterial mass from a viewpoint of storage.

BRIEF DESCRIPTION OF THE DRAWINGS

FIG. 16 is a graph which shows the amount of trichloroethylene decomposed when the cultured bacterial cells of strain MO7 of the present invention was added at one addition and at two additions.

FIG. 19 shows a flow chart of the analytical method of vinyl chloride, 1,1-dichloroethylene, cis-1,2-dichloroetylene and trans-1,2-dichloroetylene.

DETAILED DESCRIPTION

A representative bacterial strain of the present invention, strain MO7 may be isolated in the following manner. For example, an isolation source such as the soil or activated sludge is cultured in a culture medium containing phenol, and the microorganisms which propagated therein are isolated. The isolates are subsequently incubated in a medium containing trichloroethylene to select the microorganisms which have the ability of decomposing trichloroethylenea. The method of isolation of microorganisms is described in detail in Example 1.

Strain MO7 thus isolated has the following taxonomical properties:

TABLE 2

| Morphology | Coccoid, rod shaped |
|---|---|
| Gram staining | + |
| Spore forming | − |
| Motility | − |
| Behavior to oxygen | aerobic |
| Oxidase test | − |
| Catalase test | + |
| Resistance to acid | − |
| Rod-coccus cycle | + |
| Aerial mycelium | − |
| Peptide glycan type of cell wall | meso-diaminopimelic acid |
| Glycolyl test | − (acetyl type) |
| Mycolic acid | − |
| Major isoprenoid quinones | MK-8 (H4) |
| GC content of cellular DNA (mole %) | 73 (by HPLC) |

Furthermore, strain MO7 has the following properties.

| Color of colonies | No characteristic colony color formed |
|---|---|
| Elongation of cells surrounding colony | − |
| Arabinogalactan polymers of cell wall | − (#1) |

1: Estimated using an acid hydrolysate of the whole bacterial mass

Figure 1:
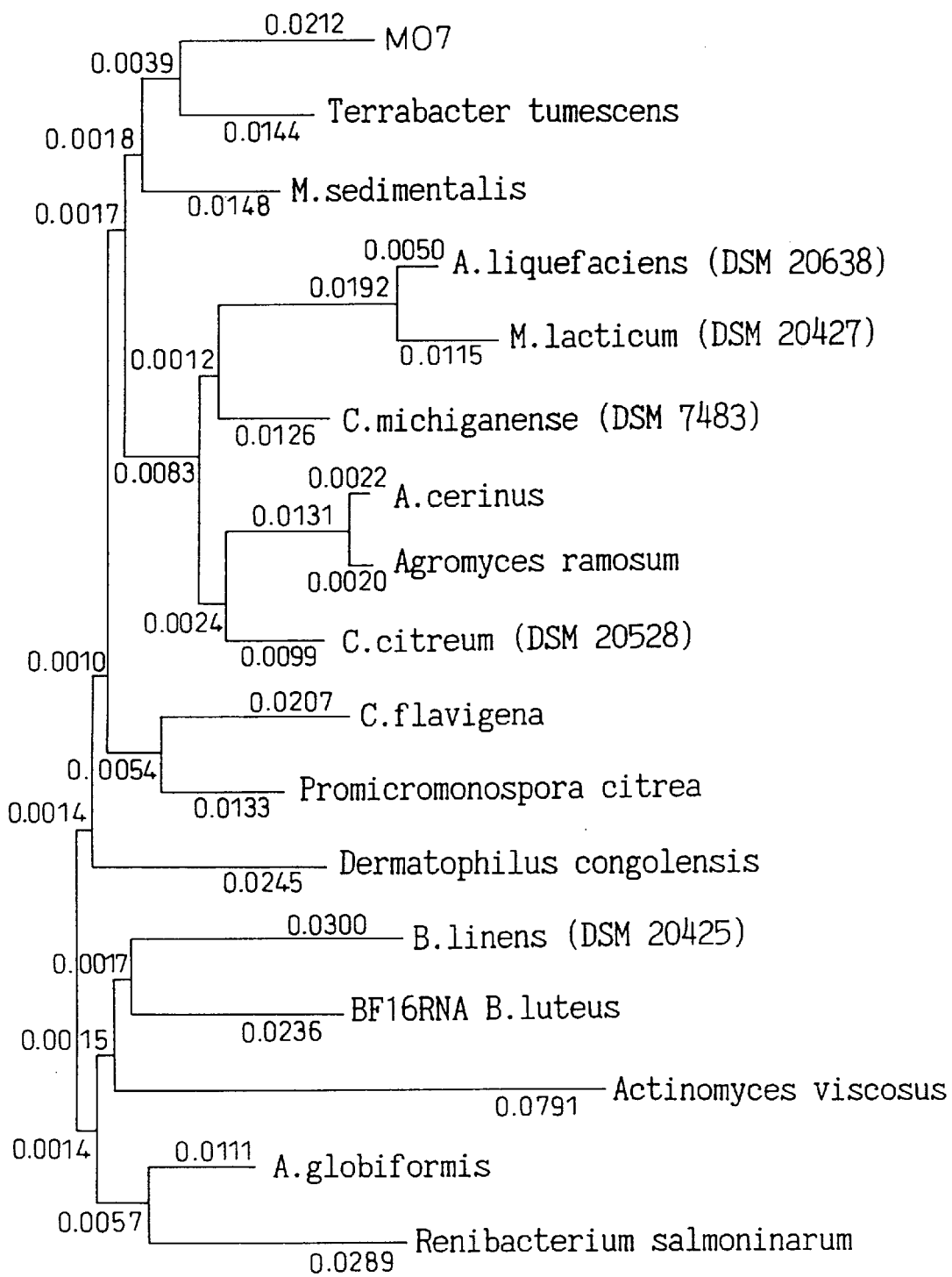
FIG. 1 shows the position of strain MO7 of the present invention in the phylogenetic tree constructed using the NJ (proximal conjugation) method.
Figure 2:
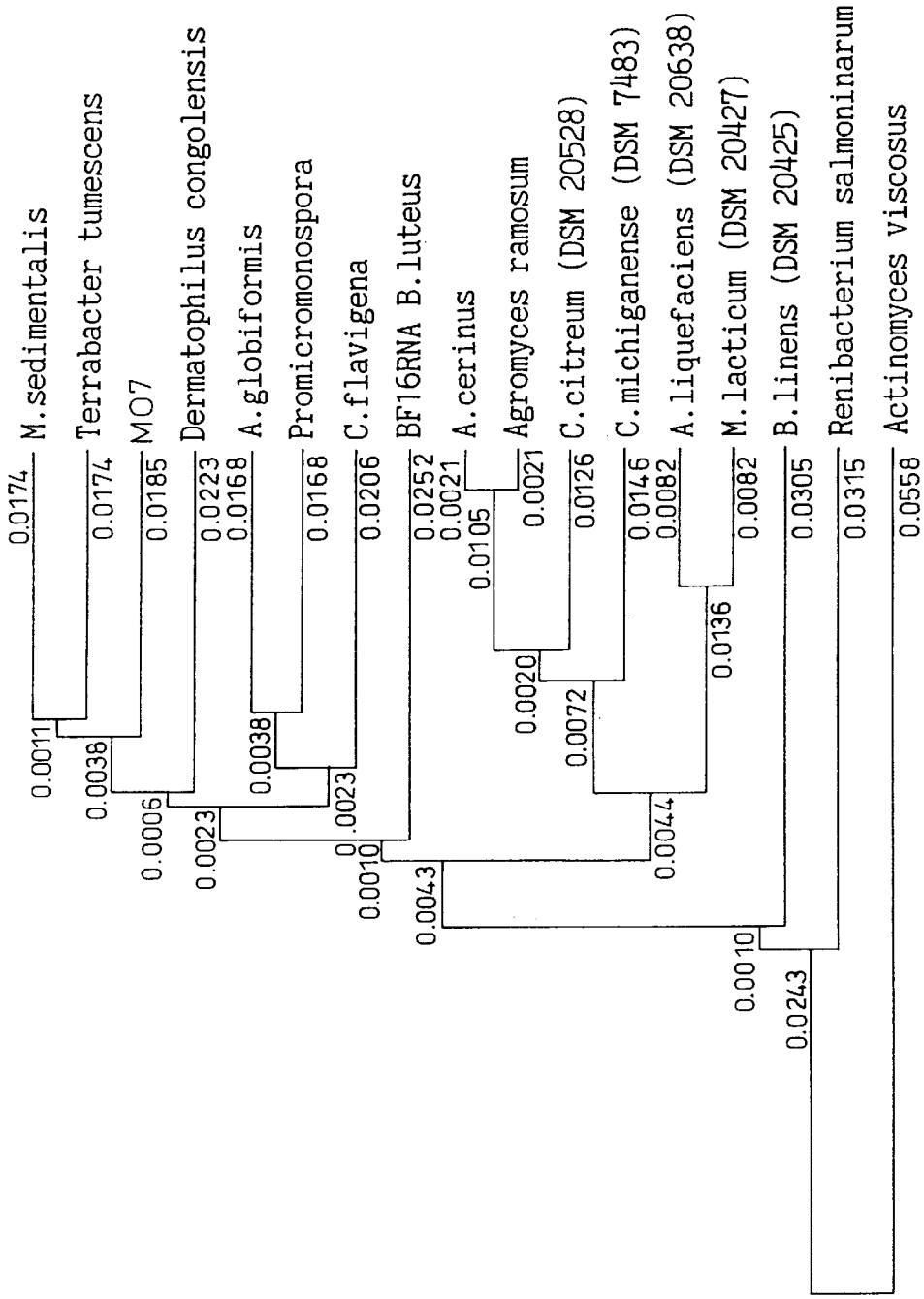
FIG. 2 shows the position of strain MO7 of the present invention in the phylogenetic tree constructed using the UPGMA (average distance) method.

The morphological and physiological characteristics of strain MO7 were investigated and the results obtained are shown in the above Table 2. Based on the results described above identification of the strain was conducted with reference to the publication (N. R. Krieg and J. G. Holt, "Bergy's Manual of Systematic Bacteriology" Vol. 1 (1984), Williams and Wilkins; J. G. Holt, N. R. Krieg, P. H. A. Senath, J. T. Staley and S. T. Williams, "Bergy's Manual of Systematic Bacteriology" Ninth edition (1984), Williams and Wilkins), with a result that the isolated strain MO7 did not conform to any known genus or species. Also 16S rRNA gene was cloned and its sequence was compared with those of the known organisms to find that the closest relative thereto was *Terrabacter tumesces* as shown in FIGS. 1 and 2. However, even the organism had a homology of 95% at most and thus it was concluded that the isolated strain does not belong to said genus. The bacterial strain of the present invention, therefore, was confirmed to be a new genus which is different from any of the known bacteria.

In the method of the present invention, organic halogenated compounds and/or aromatic compounds are decomposed by allowing the bacterium of the present invention to act on said organic halogenated compounds and/or said aromatic compounds. The organic halogenated compounds decomposed by the bacterium of the present invention include trichloroethylene, dichlcroethylene, and vinyl chloride. From a practical point of view, trichloroethylene is most important. As the aromatic compounds there are mentioned phenolic compounds, for example phenol.

In accordance with one embodiment of the present invention, there is provided a method for decomposing organic halogenated compounds in the soil, waste waters, or other waste products, said method comprising adding the culture of the bacterium of the present invention to said soil, waste waters, or other waste products. The bacterial culture as used herein includes the culture liquid itself obtained by culturing the bacterium of the present invention, a cultured bacterial mass isolated from said culture liquid, or a sterilized bacterium in said culture liquid or a sterilized cultured bacterial mass which was isolated.

For culturing of the bacterium of the present invention, any culture medium in which said bacterium can propagate may be used. The culture medium may contain a carbon source such as glucose or sucrose, an organic nitrogen source such as yeast extract, peptone or meat extracts, or an inorganic nitrogen source such as an ammonium salt or nitrate. It may further contain inorganic salts comprising cations such as potassium ion, sodium ion, calcium ion, or magnesium ion, and anions such as chlorine ion, sulfate ion, or phosphate ion. The concentration of the carbon source, though varying depending upon the species, is in the range of about 0.1 to about 1%, and that of the nitrogen source, though varying depending upon the species, is in the range of about 0.01 to about 1%. And that of the inorganic salts, though varying depending upon the species, is in the range of about 0.001 to about 0.1%.

Culturing is preferably conducted by an aerobic liquid culture. The aerobic condition may be secured by a conventional means such as aeration, agitation, aeration and agitation, or shaking. In order to induce the decomposing ability of organic halogenated compounds such as trichloroethylene and that of aromatic compounds such as phenol, an aromatic compound such as phenol is preferably added to the culture medium. In this case, an aromatic compound such as phenol may be added in addition to the other carbon source, or an aromatic compound such as phenol may be added as the only carbon source. The amount of phenol etc. added to the medium is preferably in the range of about 100 ppm to bout 1000 ppm.

In a case where the microorganism of the present invention is used in the form of a bacterial mass, said bacterial mass may be isolated by a conventional means of separating bacterial cells such as centrifugation. When the bacterial mass is stored prior to use, it may be converted into the form of a freezed or dried bacterial mass. In this case, a conventional means for drying a bacterial mass may be employed such as freeze-drying, or spray-drying. In the practice of the present invention, a sterilized culture or a sterilized bacterial mass may be used in order to minimize its effect on the environment (the microbial phase). As a means of sterilization for this purpose, a conventional method such as ultra-violet irradiation to the living bacterial mass may be used. Such sterilized cells or cultures are also encompassed in the "culture" as defined in the present invention.

When the culture of the present invention is added to the subject to be treated, it is preferred to add a living bacterial mass in an amount of $10^6$ to $10^9$ cells/g of the subject to be treated, or a sterilized bacterial mass having the corresponding ability of decomposing organic halogenated compounds.

As a means to allow the microorganism of the present invention to act on an organic halogenated compound such as trichloroethylene, the culture of the present invention need only be added to and mixed with the subject to be treated in order to decompose the organic halogenated compounds contained in the solid such as the soil or the liquid such as waste waters (referred to herein as the subject to be treated).

In accordance with another embodiment of the present invention, organic halogenated compounds such as trichloroethylene contained in the subject to be treated can be decomposed by inoculating the microorganism of the present invention to the subject to be treated such as the soil, waste waters, or other waste products, and then allowing said organism to propagate therein. Thus, the present invention also provides a method for decomposing organic halogenated compounds in the soil, waste waters, or other waste products containing said organic halogenated compounds, said method comprising inoculating the bacterium of the present invention to said soil, waste waters, or other waste products, adding an aromatic compound, an degradable carbon source, or a mixture thereof to the soil, waste waters, or other waste products, and then culturing said inoculated microorganism.

In this case, saccharides, for example glucose, is preferred as the degradable carbon source. The amount of such carbon source is about 0.1 to about 1% relative to the amount of the subject to be treated. Furthermore, when an aromatic compound is added to the subject to be treated, said aromatic compound need to be added. As an aromatic compound, phenol, cresol, and the like may be used. In this case, when the aromatic compound which was added remains after the decomposition of such organic halogenated compounds, it will cause another environmental pollution. Therefore, the addition of an excessive amount of the aromatic compound is not desirable and the amount of the aromatic compound to be added is preferably about 100 to about 500 ppm relative to the subject to be treated.

The inventors have found that the cultured bacterial mass of the present invention prepared as mentioned above, whether it is a living or a sterilized bacterial mass, retains the ability of decomposing organic halogenated compounds and/or aromatic compounds. Thus, the present invention provides a method for decomposing organic halogenated compounds and/or aromatic compounds in the soil, waste waters, or other waste products containing organic halogenated compounds and/or aromatic compounds, in which said sterilized cultured bacterial mass of a microorganism capable of decomposing organic halogenated compounds and/or aromatic compounds is added to said soil, waste waters, or other waste products.

The sterilization methods used includes Ultra violet irradiation, ethylene oxide treatment, radiation, and the like. The sterilized product has an unexpected characteristics of having a higher stability during storage with regard to the ability to decompose organic halogenated compounds.

The present invention also provides a decomposition agent of organic halogenated compounds and/or aromatic compounds, said agent comprising a cultured fo the bacterium of the present invention. The culture is preferably a cultured bacterial mass, which may be a living bacterial mass or a sterilized bacterial mass. Sterilization treatment is carried out by ultra violet irradiation, ethylene oxide treatment, radiation, or another method as described above. From a viewpoint of storage etc. the decomposition agent of the present invention is preferably in the freezed or dried form, which dried product may be obtained according to a conventional method as mentioned above.

The strain MO715, a representative mutant of the present invention (referred to hereinafter as the constitutive mutant) which does not require an aromatic compound (such as phenol) for inducing the activity of trichloroethylene decomposition can be isolated as follows: the strain MO7 is mutated by the action of ultra violet, radiation, or a chemical substance such as nitrosoguanidine which has a mutagenic activity and constitutive mutants are selected from the resulting mutants. The method of isolation of microorganisms is explained in detail in Example 18.

The cultivation of the constitutive mutant of the present invention may be carried out in the same manner as for the parent strain MO7 except that the cultivation of the former does not require an aromatic compound for the induction of the ability of decomposing trichloroethylene. The degradable carbon source for cultivation is preferably a saccharide such as glucose, or an amino acid such as glutamic acid. The method of using it is also the same as for the parent strain MO7 except that the cultivation of the former does not require an aromatic compound for the induction of the ability of decomposing trichloroethylene. It should be noted that the living bacterial mass or the sterilized bacterial mass thereof has the same effect as the parent strain MO7 with regard to the ability of decomposing organic halogenated compounds.

The above-mentioned microorganism, the strain MO7, has been internationally deposited on Aug. 12, 1996, with the National Institute of Bioscience and Human-Technology, Agency of Industrial Science and Technology, MITI, as FERM BP-5624 under the provisions of the Budapest Treaty. And the above-mentioned microorganism, the strain MO715, has also been internationally deposited on Apr. 24, 1997, with the National Institute of Bioscience and Human- Technology, Agency of Industrial Science and Technology, MITI, as FERM BP-5928 under the provisions of the Budapest Treaty. The National Institute of Bioscience and Human-Technology is located at "1-1, Higashi, Tsukuba, Ibaraki, 305 Japan.

EXAMPLES

The invention will be understood more readily with reference to the following examples; however these examples are intended to illustrate the invention and are not to be construed to limit the scope of the invention.

Example 1. Isolation of the MO7 Strain as well as Cloning and Sequencing of 16S rDNA Thereof The microorganisms for use in the present invention were isolated from the activated sludge taken at the waste water treatment plant in Aichi prefecture, Japan, in the following manner. A 0.1 ml aliquot of the harvested activated sludge collected was inoculated into 6 ml of the NMS medium containing 1% (v/v) of a vitamin solution (its composition is shown in Table 5) in a 30 ml vial, to which was added 500 ppm of phenol.

The vial was plugged with a butyl rubber septum and sealed with an aluminum cap, which was then cultured at 30° C. under shaking at 160 r.p.m. for a period of from several days to about a dozen days. The culture in which turbidity, even the slightest turbidity, was observed was passaged to the same medium and subsequently cultured under shaking. The passage was repeated for a total of four times. After the fourth passage is over, the culture medium was diluted as appropriate and plated onto the agar plate prepared by adding 1.5% agar to the NYG medium (its composition is shown in Table 5) containing 500 ml phenol. The colonies which appeared were picked onto the agar plate and incubated. This operation was repeated for several times to isolate the microorganisms. In addition to the above NYG medium, another medium such as a nutrient medium can be used after selecting the optimum condition thereof for culturing of microorganisms.

TABLE 3

| NMS medium | |
|---|---|
| Magnesium sulfate heptahydrate | 1.0 g |
| Calcium sulfate dihydrate | 0.2 g |
| Potassium nitrate | 0.23 g |
| Ammonium sulfate | 0.65 g |
| Potassium dihydrogen phosphate | 0.272 g |
| Disodium hydrogen phosphate dodecahydrate | 0.727 g |
| Trace Element Solution | 0.5 ml |
| Distilled water | 1 liter |
| The Trace Element Solution | |
| EDTA disodium dihydrate | 500 mg |
| Iron (II) sulfate heptahydrate | 200 mg |
| Zinc sulfate heptahydrate | 10 mg |
| Manganese (II) chloride tetrahydrate | 3 mg |
| Boric acid | 30 mg |
| Cobalt (II) chloride hexahydrate | 20 mg |
| Nickel (II) chloride hexahydrate | 2 mg |
| Sodium molybdenum dihydrate | 3 mg |
| Distilled water | 1 liter |

\* Trace Element Solution was separately sterilized and added after the other ingredients were sterilized.

TABLE 4

| Vitamin solution | |
|---|---|
| Thiamine hydrochloride | 3 mg |
| p-amino benzoic acid | 13 mg |
| Adenine | 1000 mg |
| NAD | 250 mg |
| Vitamin B12 | 10 mg |
| Thiamine diphosphate | 100 mg |
| Distilled water | 1 liter |

TABLE 5

| NYG medium | |
|---|---|
| Yeast Extract | 0.5 g |
| Glucose | 0.18 g |
| NMS medium | 1 liter |

The isolated microorganism was inoculated into 10 ml of the MNS medium containing 0.05% of yeast extract and 500 ppm of phenol in a 18 cm test tube by picking a colony on the agar plate for isolation using a platinum loop. After culturing at 30° C. under shaking at 130 r.p.m. for 5 days, the bacterial mass was harvested by centrifugation at 5000 r.p.m. for 10 minutes, and then resuspended into 4 ml of the NMS medium. The suspension of the bacterial mass was placed in a 20 ml vial and trichloroethylene was added in such an amount that it became 30 ppm after all ingredients were dissolved in the liquid phase simultaneously. The vial was plugged with a Teflon-coated butyl rubber septum and sealed with an aluminum cap. After culturing overnight at 30° C., the gas phase in the vial was analyzed by a gaschromatograph equipped with a FID or an ECD detector.

From the results obtained, a bacterial strain having a high ability of decomposing trichloroethylene was selected and characterized for the morphological and physiological properties to obtain the results as shown in Table 2.

Based on said results, identification was carried out with reference to the publication (N. R. Krieg and J. G. Holt, "Bergy's Manual of Systematic Bacteriology" Vol. 1 (1984) Williams and Wilkins, and J. G. Holt, N. R. Krieg, P. H. A. Senath, J. T. Stanley and S. T. Williams, "Bergy's Manual of Determinative Bacteriology" Ninth edition (1984) Williams and Wilkins) to find that this bacterial strain does not belong to any of the known genera or species. The bacterial strain was designated as the MO7 strain and was internationally deposited on Aug. 12, 1996, with the National Institute of Bioscience and Human-Technology, Agency of Industrial Science and Technology, MITI, as FERM BP-5624 under the provisions of the Budapest Treaty.

Furthermore, the sequence of 16S rDNA of the microorganism of the present invention was determined and compared with that of the known microorganisms. The results are outlined hereinbelow.

The 16S rDNA of the microorganism of the present invention was amplified using PCR according to the method of Hiraishi (Journal of Japanese Society for Microbiological Ecology, vol. 10 (1): 31–42, 1995). The primers used for the PCR had the base sequence: 5'-GAG TTT GAT CCT GGC TCA G-3' (SEQ ID No: 1), and 5'-AGA AAG GAG GTG ATC CAG CGG CAG GTT-3' (SEQ ID No: 2). PCR was conducted using a thermal cycler (Perkin Elmer) according to the following program: i.e., preheating at 90° C. for 30 seconds, 30 cycles of 96° C. for 60 seconds/55° C. for 120 seconds/72° C. for 180 seconds, and heating at 72° C. for 300 seconds.

The amplified PCR fragment was purified using QIAquick (Quiagen) and sequenced by a method which utilized a PCR directly as a template according to the method of Hiraishi (Journal of Japanese Society for Microbiological Ecology, vol. 10 (2): 81–102, 1995). The primers used for the sequence reaction had the base sequence: 5'-GAG TTT GAT CCT GGC TCA G-3' (SEQ ID No: 1), 5'-GGC CGG ACG GGT GAG T-3' (SEQ ID No: 3), 5'-TAC GGG AGG CAG CAG-3' (SEQ ID No: 4), 5'-CTG CCA GCA GCC GCG CG-3' (SEQ ID No: 5), 5'-G ATT AGA TAC CCT GGT AG-3' (SEQ ID No: 6), 5'-ACT CAA AGG AAT TGA CGG-3' (SEQ ID No: 7), 5'-GCA ACG AGC GCA ACC C-3' (SEQ ID No: 8), or 5'-TGT ACA CAC CGC CCG T-3' (SEQ ID No: 9). PCR was conducted using the Dye terminator cycle sequencing kit (Perkin Elmer) according to the protocol instructed in the kit. Sequenced samples were subjected to electrophoresis and sequence analysis using the ABI373A Sequencer (Perkin Elmer). The base sequence determined by these procedures of the 16S rDNA of the microorganism of the present invention is shown in Table 6 (SEQ ID NO:10).

TABLE 6

```
Sequence     1466 BP;    352 A;    355 C;    288 T;    467 G.
AACGCTGGCG GCGTGCTTAA CACATGCAAG TCGAACGGTG AAGCTTGGAG CTTGCTTCGA
GTGGATCAGT GGCGAACGGG TGAGTAACAC GTGAGCAACC TGCCCCAGAC TCTGAATAA
GCGCTGGAAA CGGCGTCTAA TACTGGATAT GTGACGGACC TGCATGGGTA CCGTCTGGAA
AGTTTTTCGG TTTGGGATGG GCTCGCGGCC TATCAGCTTG TTGGTGAGGT AATGGCTCAC
CAAGGCGACA ACGGGTANCC GGCCTGAGAG GGCGACCGGC CACACTGGGA CTGAAACACG
GCCCAAACTC CTACGGGAGG CACCAGTGGG GAAATATTGC ACAATGGGCG AAAGCCTGAT
GCAGCGACGC CGCGTGAGGG ATGACGGCCT TCGGGTTGTA AACCTCTTTC AGCAGGGAAG
AAGCGAAAGT GACGGTACCT GGAGAATAAG CACCGGCTAA CTACGTGCCA GCAGCCGCGG
TAATACGTAG GGTGCGAGCG TTGTCCGGAA TTATTGGGCG TAAAGAGCTT GTAGGCGGTT
TGTCGCGTCT GCTGTGAAAA TCCGGGGCTC AACCCCGGAC TTGCAGTGGG TACGGGCAGA
CTAGAGTGTG GTAGGGGAGA CTGGAATTCC TGGTGTAGCG GTGAAATGCG CAGATATCAG
GAGGAACACC GATGGCGAAG GCAGGTCTCT GGGCCACTAC TGACGCTGAG AAGCGAAAGC
ATGGGGAGCG AACAGGATTA GATACCCTGG TAGTCCATGC CGTAAACGTT GGGCGCTAGG
TGTGGGACTC ATTCCACGAG TTCCGTGCCG CAGCTAACGC ATTAAGCGCC CCGCCTGGGG
CAGTACGGCC GCAAGGCTAA AACTCAAAGG AATTGACGGG GGCCCGCACA AGCGGCGGAG
CATGCGGATT AATTCGATGC AACGCGAAGA ACCTTACCAA GGGTTGACAT ATACCGGAAA
CTTCCAGAGA TGGTTGCCCC CTTTGGGTCG GTATACAGGT GGTGCATGGT TGTCGTCAGC
TCGTGTCGTG AGATGTTGGG TTAAGTCCCG CAACGAGCGC AACCCTCGTT CTATGTTGCC
AGCACGTCAT GGTGGGGACT CATGGAAGAC TGCCGGGGTC AACTCGGAAG AAGGTGGGGA
TGACGTCAAA TCATCATGCC CCTTATGTCT TGGGQTTCAC GCATGCTACA ATGGCCGGTA
CAAAGGGCTG CGATACCGCA AGGTGGAGCG AATCCCCAAA AAACCGGTCT CAGTTCGGAT
TGGGGTCTGC AACTCGACCC CATGAAGTCG GAGTCGCTAG TAATCGCAAA TCAGCAACGC
TGCGGTGAAT ACTTTCCCGG GCCTTGTACA CACCGCCCGT CAAGTCACGA AAGTTCGGTA
ACACCCGAAG CCGGTGGCCC AACCCTTGTG GGGGGAGCCG TC
```

The base sequence thus obtained was compared with the data in DNA database at the National Institute of Heredity (DDBJ+DDBJ NEW). Search of the homologous bacterial strains was conducted using the program "blast" to default value and at first, 50 species were selected which had the highest homology. From among them the bacterial strain (genus Mycobacterium which has the property of producing mycolic acid) which were believed to be definitely different from the results of physiological taxonomic tests were excluded. Then the multiple alignment analysis with the rest of the bacterial strains and the type strains of the genera which are thought to be closely related were conducted.

From the results obtained, a phylogenetic tree was constructed using the NJ (proximal conjugation) method (FIG. 1) or the UPGMA (average distance) method (FIG. 2) (alignment was conducted after the sequences at the 5'-ends were aligned). The most closely related organism turned out to be *Terrabacter tumescens* (the phylogenic tree includes *Mycobacterium sedimentalis* for reference). The closely related bacterial strains (microorganisms belonging to the same cluster) were subjected again to homology search using Genetryx-Mac 8.0. But, the homology of the gene of even the closest *Terrabacter tumescens* was up to 95% and it was judged not to be the same genus. Therefore, it was confirmed that the microorganism of the present invention is a new microorganism different from any of the knowm microorganism.

The microorganism decomposes about 50% of trichloroethylene at high concentrations of about 100 ppm contaminated in the culture medium, and completely decomposes about 30 ppm of trichloroethylene in 24 hours. In order to decompose trichloroethylene in association with the propagation of the microorganism, it is necessary to add at least one aromatic compound such as phenol in the culture medium (medium, soil, water, etc.) containing trichloroethylene.

The microorganism for use in the present invention will be explained in more detail with reference to the following examples.

Example 2

Into 100 ml of the NMS medium containing 0.05% yeast extract and 500 ppm of phenol contained in a 500 ml Erlenmeyer flask was inoculated with a platinum loopful of the colony of the microorganism of the present invention that had been stored by passage on the agar plate of 1.5% agar added to the NYG medium containing 500 ppm phenol, or 1.0 ml of the preculture liquid obtained by culturing overnight under shaking the microorganism of the present invention in the NYG medium containing 500 ppm of phenol at 30° C. After culturing under shaking at 30° C. at 130 r.p.m. for 3 days, the bacterial mass was harvested by centrifugation at 5000 r.p.m. for 10 minutes and then resuspended into the NMS medium having an amount equal to the culture medium.

The $OD_{600}$ of the suspension was 0.5 (the cell count was $1\times10^9$ c.f.u./ml). 4 ml of the suspension of the bacterial mass was dispensed in a 20 ml vial and trichloroethylene was added thereto in such an amount that it became 10, 50, or 30 ppm after all the ingredients were dissolved in the liquid phase. The vial was plugged with a Teflon-coated butyl rubber septum and sealed with an aluminum cap. After culturing overnight at 30° C. under shaking, the gas phase in the vial was regularly analyzed by a gaschromatograph equipped with an ECD detector.

Figure 3:
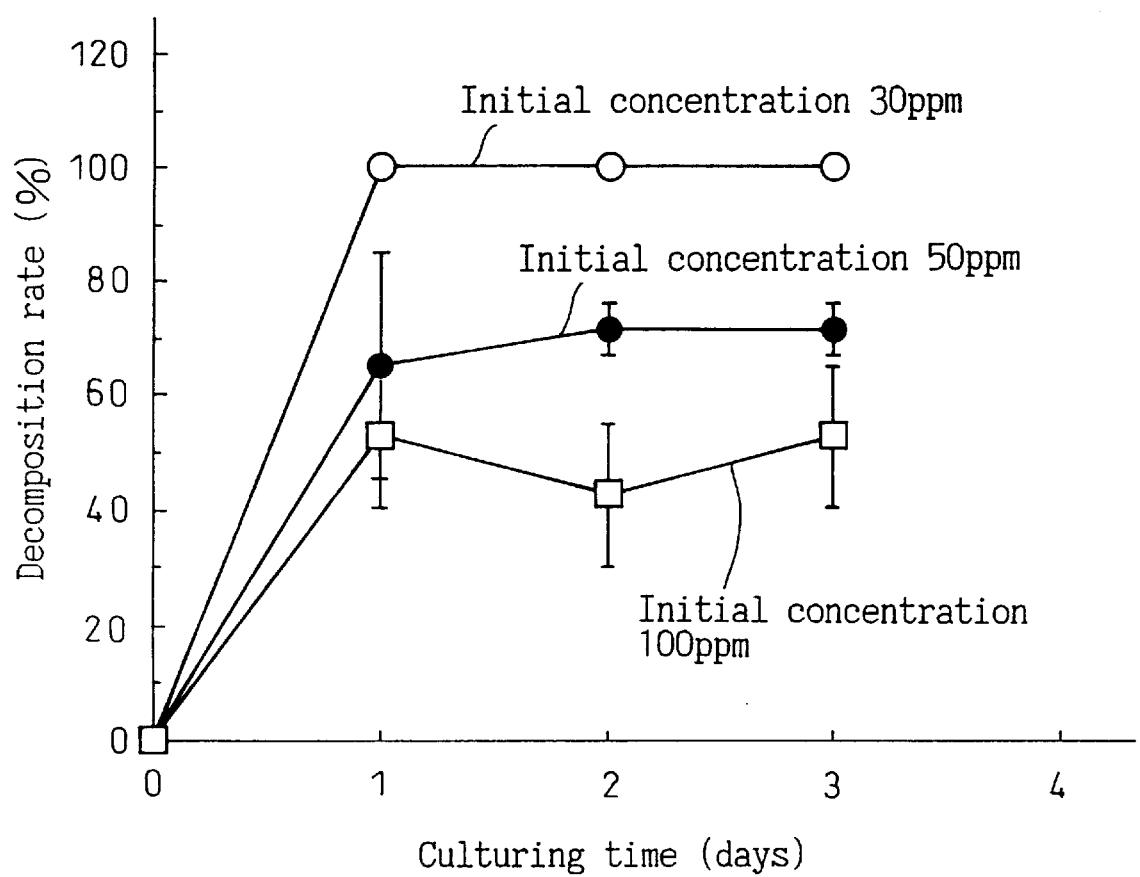
FIG. 3 is a graph which shows the effect of the initial concentrations of trichloroethylene on the decomposition efficiency, obtained using strain MO7 of the present invention.

The result is shown in FIG. 3. The present microorganism completely decomposed trichloroethylene in 24 hours. Trichloroethylene at such a high concentration of 50 ppm and 100 ppm was decomposed by 70% and 50%, respectively in 24 hours. Even when the initial concentration of trichloroethylene as high as 50 and 100 ppm, the amount of trichloroethylene decomposed by the present microorganism was not reduced as compared to that when the initial concentration of trichloroethylene was 30 ppm, indicating that the present microorganism is resistant to decomposition inhibition even in the presence of a high concentration of trichloroethylene. Since there has been no reports which demonstrate that as high as 100 ppm of trichloroethylene was decomposed by a microorganism, the decomposition ability of the present microorganism is believed to be extremely high.

Example 3

Figure 4:
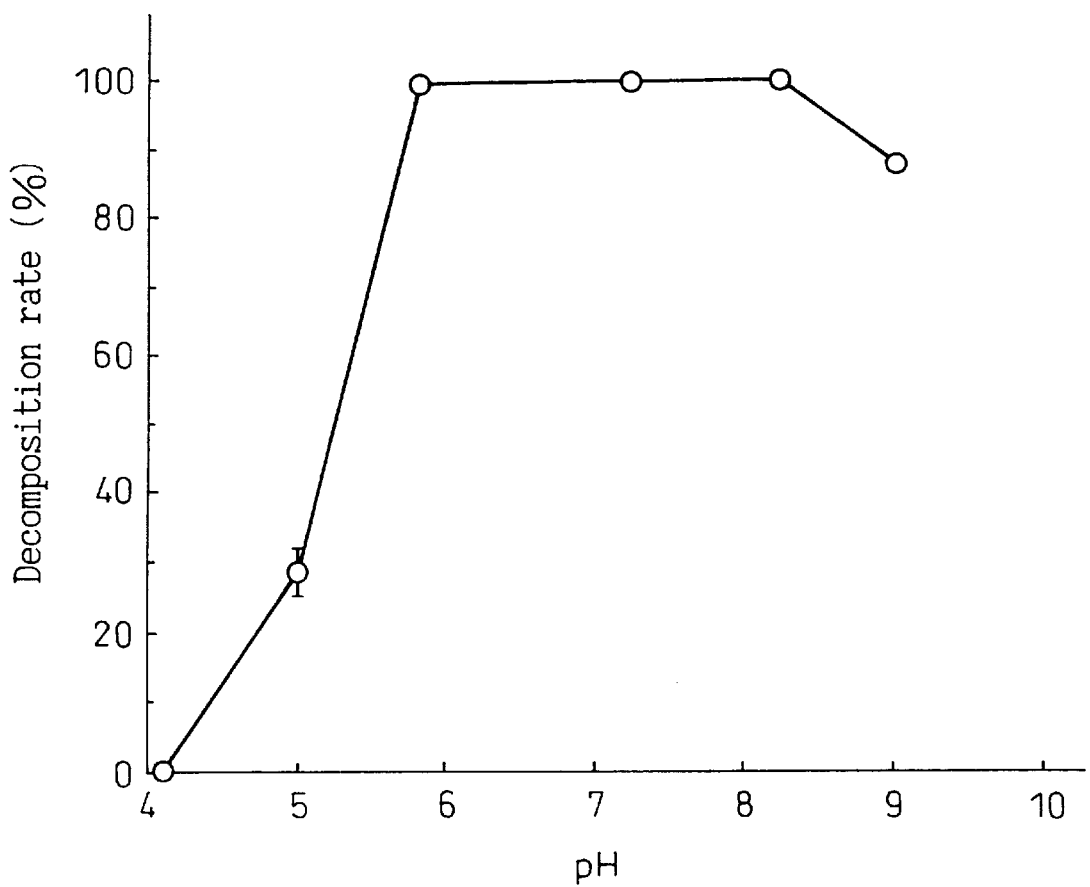
FIG. 4 is a graph which shows the effect of pH on the decomposition efficiency of trichloroethylene (an initial concentration of 30 ppm), obtained using strain MO7 of the present invention.

The bacterial mass cultured in the same method as in Example 2 was harvested by centrifugation at. 5000 r.p.m. for 10 minutes and then resuspended to each of the M9 medium ($Na_2HPO_4 \cdot 7H_2O$ 12.8 g/l, $KH_2PO_4$ 3 g/l, NaCl 0.5 g/l, $NH_4Cl$ 1.0 g/l) prepared in varying pH's at an amount equal to that of the culture liquid. 4 ml of the suspension of the bacterial mass was dispensed in a 20 ml vial and trichloroethylene was added thereto in such an amount that it became 30 ppm after all the ingredients were dissolved in the liquid phase. The vial was plugged with a Teflon-coated butyl rubber septum and sealed with an aluminum cap. After culturing overnight at 30° C. under shaking, the gas phase in the vial was regularly analyzed by a gaschromatograph equipped with an ECD detector. As shown in FIG. 4, the result indicated that at pH 5 or lower the activity is extremely decreased, whereas at pH 6 to 9 the efficiency of decomposition was as high as 100% and the activity decreased very slightly to about 90% even at pH 10.

Thus, it turned out that the optimum pH of trichloroethylene decomposition by a resting bacterial mass of the MO7 strain was between 6 and 9, indicating that a high decomposition activity is exhibited at high pH conditions. Trichloroethylene oxide produced by aerobic decomposition of trichloroethylene spontaneously decomposes at an alkaline environment, producing innoxious glyoxylic acid etc. On the other hand, in an acid condition it spontaneously decomposes to produce halo acid. Accordingly, the aerobic decomposition of trichloroethylene by a microorganism is preferably conducted at an alkaline environment. The present microorganism is very useful for decomposition of trichloroethylene at an alkaline environment, since it shows a high decomposition activity at a high pH condition.

Example 4

The bacterial mass cultured in the same method as in Example 2 was harvested by centrifugation at 5000 r.p.m. for 10 minutes and then suspended into the same volume of the NMS medium as the culture liquid. 4 ml of the suspension of the bacterial mass was dispensed in a 20 ml vial and trichloroethylene was added thereto in such an amount that it became 30 ppm after all the ingredients were dissolved in the liquid phase. The vial was plugged with a Teflon-coated butyl rubber septum and sealed with an aluminum cap. It was cultured under shaking in an incubator each set at a different temperate. The residual concentration of trichloroethylene was regularly monitored by analyzing the gas phase in the vial with a gaschromatograph equipped with an ECD detector.

Figure 5:
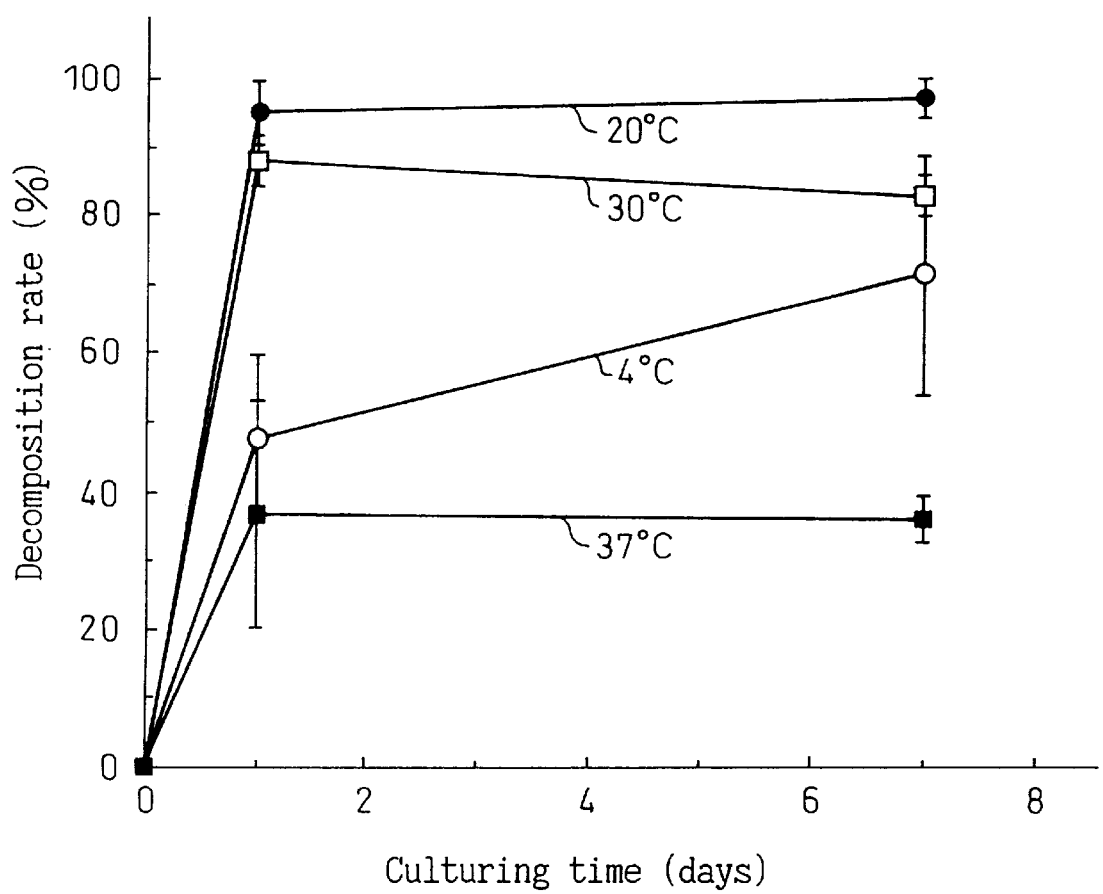
FIG. 5 is a graph which shows the effect of the temperature on the decomposition efficiency of trichloroethylene (an initial concentration of 30 ppm), obtained using strain MO7 of the present invention.

As shown in FIG. 5, the result indicated that the decomposition of trichloroethylene proceeded slowly over 7 days at 4° C. At 37° C., the decomposition ceased in a day and the decomposition efficiency was low. On the other hand, 80 to 90% was decomposed in a day at 20° C. and 30° C. But decomposition activity was about 10% higher at 20° C. than at 30° C. The temperature of the underground soil where contamination by trichloroethylene etc. is causing a problem is said to be stable at 15 to 20° C. However, in most of the reports on the trichloroethylene-decomposing microorganisms decomposition activity was evaluated at 30° C. which is higher than the temperature of the soil, and very few studies have demonstrated that decomposition activity at the same temperature as the soil environment was maintained at a similar level to that at the evaluation experiments.

Since the reaction rate of the enzymatic reaction representing the basic reaction of microbial decomposition usually decreases by one-half with a temperature reduction of 10° C., it is estimated that the decomposition rate of trichloroethylene by a microorganism in the soil having a temperature lower than that at the evaluation experiment is reduced. The present microorganism was demonstrated to have a high practical characteristics without showing reduction in decomposition activity at the same temperature as the soil environment, though the mechanism thereof is unknown.

Example 5

The bacterial mass cultured in the same method as in Example 2 was harvested by centrifugation at 5000 r.p.m. for 10 minutes and then suspended to the same volume of the NMS medium as that of the culture liquid. The suspension of the bacterial mass was placed in a petri dish and spread to a thickness of about 1 mm and then sterilized under irradiation of a 15 W ultra violet lamp with a wavelength of 260 nm for not less than 60 seconds at a distance of 40 cm from the light source. 4 ml of the suspension of bacterial mass after sterilization was dispensed in a 20 ml vial and trichloroethylene was added thereto in such an amount that it became 30 ppm after all the ingredients were dissolved in the liquid phase. The vial was plugged with a Teflon-coated butyl rubber septum and sealed with an aluminum cap. It was cultured under shaking at 30° C., and the gas phase in the vial was regularly analyzed with a gaschromatograph equipped with an ECD detector.

Figure 6:
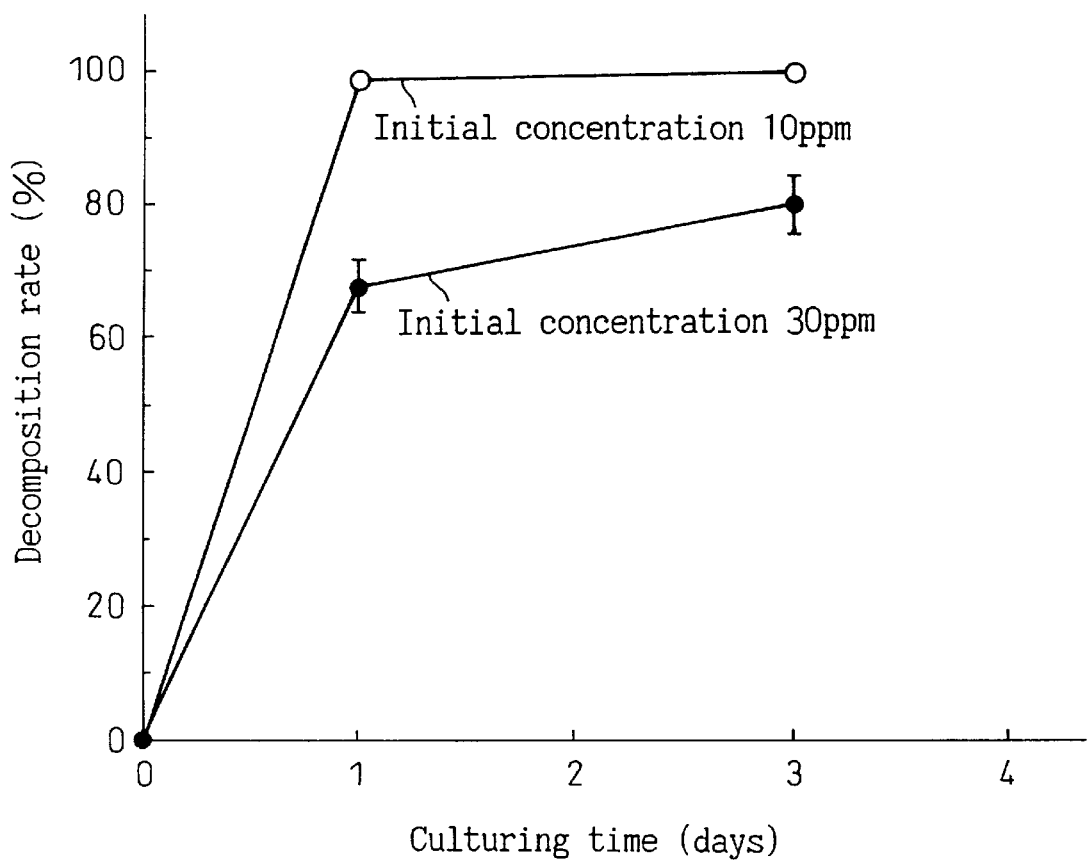
FIG. 6 is a graph which shows the effect of the initial concentration of trichloroethylene on the decomposition efficiency of trichloroethylene (an initial concentration of 30 ppm), obtained using the dead bacterial cells (sterilized with ultra violet irradiation) of strain MO7 of the present invention.
Figure 7:
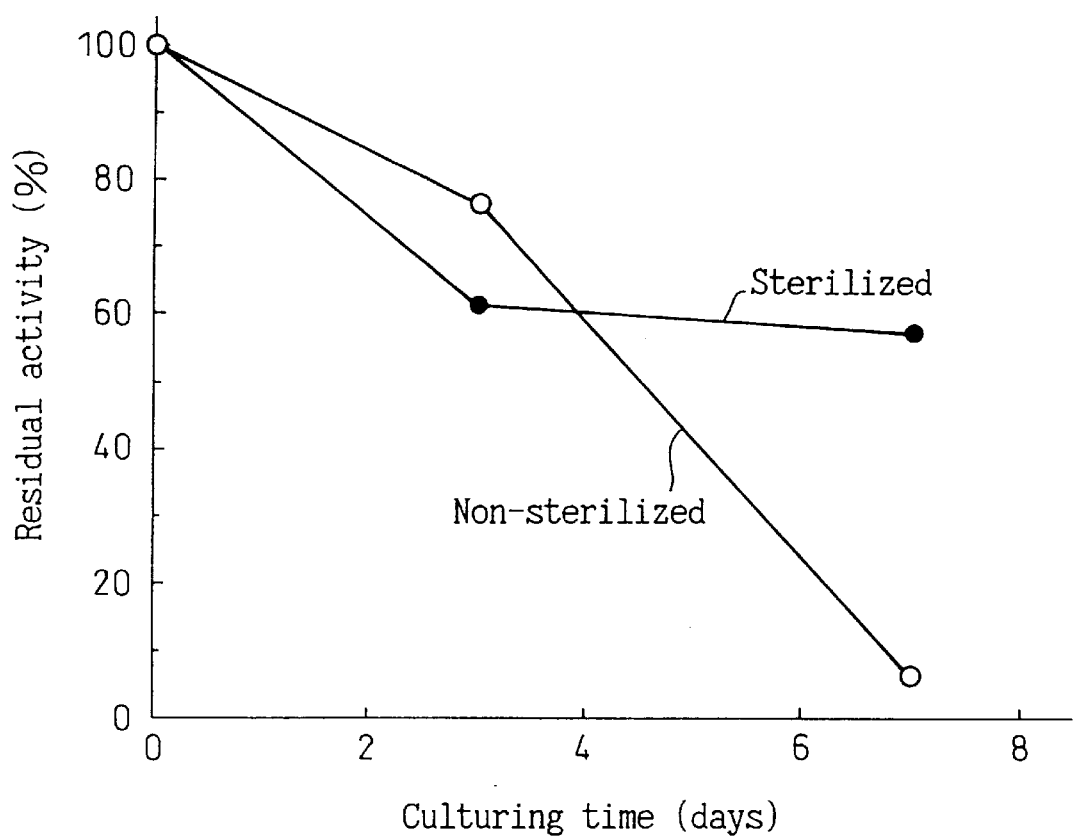
FIG. 7 is a graph which shows a time course of the residual activity of decomposing trichloroethylene using the sterilized (with ultra violet irradiation) and the non-sterilized cultured bacterial cells of strain MO7 of the present invention.

As shown in FIG. 6, the result shows that the bacterial mass after sterilization retains 80% or more of the trichloroethylene-decomposition activity of the living bacterium. Furthermore, in an experiment in which the suspension of sterilized bacterial mass at an amount of 1/100 that of the NYG medium was inoculated or the suspension was plated as it was onto the NYC: agar medium and cultured at 30C, neither increase in turbidity of the culture liquid nor colony formation were observed, and thereby it was confirmed that there was complete sterilization.

The residual activity of the suspension of the sterilized bacterial mass when stored at 4° C. was almost the same as that of the living bacterial mass at three days of storage and said suspension had a much higher activity than that of the living bacterial mass at seven days of storage. The results reveal that although the initial activity of the dead bacterial mass is decreased to 80% of the living bacterial mass, a higher activity of decomposing trichloroethylene is retained than the living bacterial mass during storage because of a lower reduction in activity of the dead bacterial mass during storage.

By sterilizing a microorganism without destructing the boundary structure such as the cell wall of a bacterial mass with the extracellular environment, it is possible to retain coenzymes etc. which are required for decomposition reaction of trichloroethylene at concentrations necessary for expression of enzymatic activity. Thus, supply of coenzymes for maintenance of activity of trichloroethylene decomposition is not necessary and the spread of the cultured bacterial mass is only needed. It possible therefore to effect purification of trichloroethylene etc. at low cost and with a minimum effect on the ecological system.

Example 6

To 4 ml of the PH medium (see Table 8 for its composition) containing 0.05% yeast extract and 500 ppm of phenol in a 20 ml vial, the present microorganism inoculated by picking a platinum loopful of the colony of the present microorganism from the agar plate prepared by adding 1.5% agar to the NYG medium containing 500 ppm phenol, or by inoculating 0.04 ml (the cell count was $10^6$ cells/ml) of the preculture liquid obtained by culturing the present microorganism in the NYG medium containing 500 m of phenol at 30° C. overnight under shaking.

TABLE 7

| PH medium | |
| --- | --- |
| Magnesium sulfate heptahydrate | 0.2 g |
| Calcium sulfate | 0.1 g |
| Ferric chloride hexahydrate | 0.02 g |
| Dipotassium hydrogen phosphate | 1.0 g |
| Ammonium sulfate | 1.0 g |
| Sodium chloride | 0.1 g |
| Distilled water | 1 liter |

Trichloroethylene in such an amount that it became 30 ppm after all ingredients were dissolved in the liquid phase simultaneously with the inoculation and 500 ppm of phenol were added. The vial was plugged with a Teflon-coated butyl rubber septum and sealed with an aluminum cap. It was cultured under shaking at 30° C., and trichloroethylene concentration was regularly measured by analyzing the gas phase in the vial with a gaschromatograph equipped with an ECD detector. The phenol concentration was determined by filtering the culture liquid with a $0.45\mu$ filter, and adding to 1 ml of the resulting filtrate, sequentially, 0.1 ml of an aqueous solution of $K_3Fe(CN)_6$/0.1 M glycine and 1 ml of an aqueous solution of 4-amino antipyrine, which was then mixed, and measuring an absorbance at 505 nm.

Figure 8:
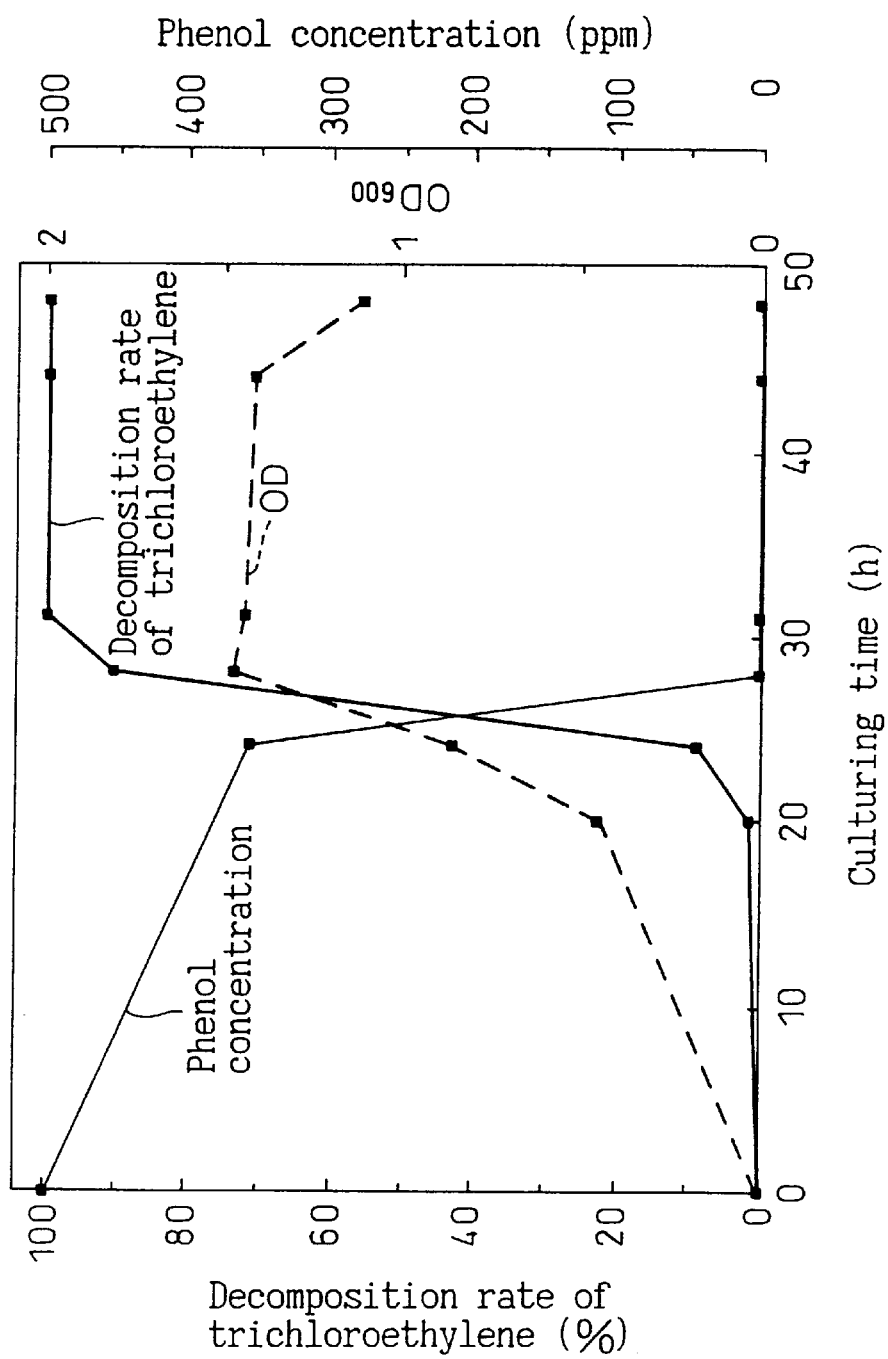
FIG. 8 is a graph which shows growth curve (OD), time course of phenol consumption and the decomposition efficiency of trichloroethylene when strain MO7 of the present invention was cultured in a medium containing phenol and trichloroethylene.

The result as shown in FIG. 8 indicates that with the propagation of the bacterial mass phenol and trichloroethylene decreases, and they were completely decomposed at 31 hours after cultivation. It was confirmed, therefore, that the present microorganism has a high activity of decomposing trichloroethylene when propagated in the presence of an aromatic compound such as phenol having the ability of inducing trichloroethylene. When compared to known microorganisms, all reports relate to decomposition of trichloroethylene at a low concentration of up to 10 ppm except for the report that *Pseudomonas cepacia* KK01 decomposes 30 ppm of trichloroethylene to 15 ppm in 2 days and the report that *Alcaligenes eutropus* KS01 (Japanese Unexamined Patent Publication No. 7(1995)-123976) decomposes completely 50 and 25 ppm of trichloroethylene in 4 days.

In the decomposition of trichloroethylene by *Alcaligenes eutropus* KS01 (Japanese Unexamined Patent Publication No. 7(1995)-123976), the amount of the microorganism inoculated to the culture medium is $10^8$ cells/ml, which is about 100 times that of the present microorganism described in Example 6. The amount of the bacterial mass required for trichloroethylene decomposition for the microorganism of the present invention is much smaller than that of *Alcaligenes eutropus* KS01. It therefore has an advantage that the cost of culturing is reduced, etc. It was also confirmed that the added and mixed phenol is decomposed to below the level of detection, thereby presenting little risk of environmental pollution by phenol which is an environmental pollutant.

The inventors have focused and investigated on the culturing method prior to inoculation in order to enhance the decomposition activity of a microorganism which has the ability of decomposing trichloroethylene in the soil and thereby to prepare a microorganism having the decomposition activity which can deal with pollution at high concentrations. As a result we have discovered that there is an optimum value of culturing time of the microorganism prior to inoculation, and that the activity of trichloroethylene decomposition can be enhanced by sequentially adding an inducer to the culture medium, and we have completed the present invention. The present invention will now be more fully explained with reference to the following examples.

Example 7

Into 100 ml of the PH medium containing 0.05% yeast extract and 500 ppm of phenol contained in a 500 ml Erlenmeyer flask was inoculated a platinum loopful of the colony of the microorganism of the present invention which had been stored by passage on the agar plate of 1.5% agar added to the NYG medium containing 500 ppm phenol, or 1.0 ml of the preculture liquid obtained by culturing the microorganism of the present invention in the NYG medium containing 500 ppm of phenol at 30° C. overnight under shaking. While culturing under shaking at 30° C. at 130 r.p.m., turbidity of the culture liquid and phenol concentration were determined in the same methods as in Example 6. The bacterial mass in the culture was harvested by centrifugation at 5000 r.p.m. for 10 minutes and then resuspended into the NMS medium having an amount equal to the culture medium. The $OD_{600}$ of the suspension was 0.2 (the cell count was $1\times10^8$ c.f.u./ml).

Figure 9:
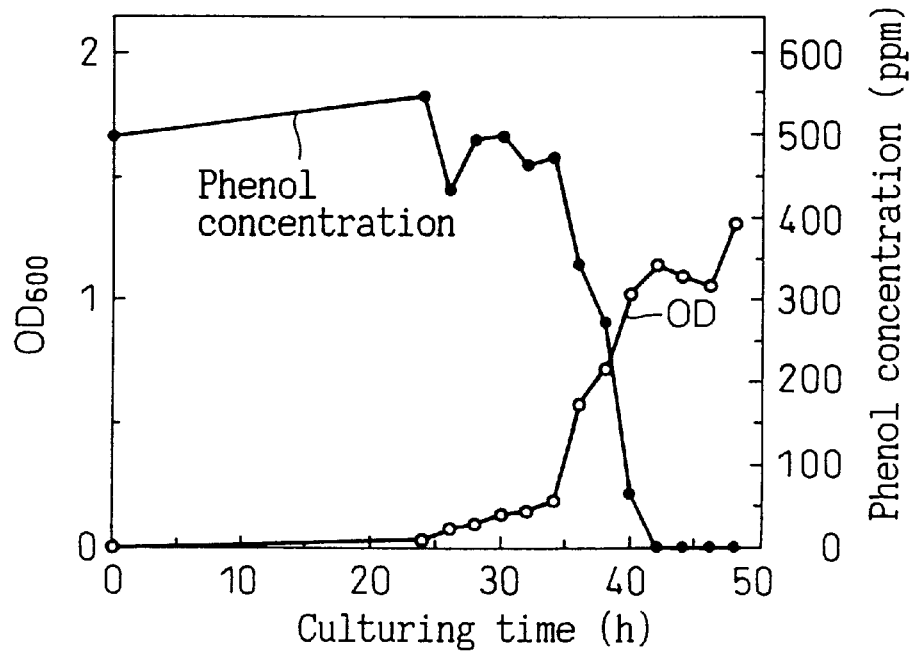
FIG. 9 is a graph which shows growth curve (OD) and a time course of phenol consumption when strain MO7 of the present invention was cultured in a culture medium containing phenol.
Figure 10:
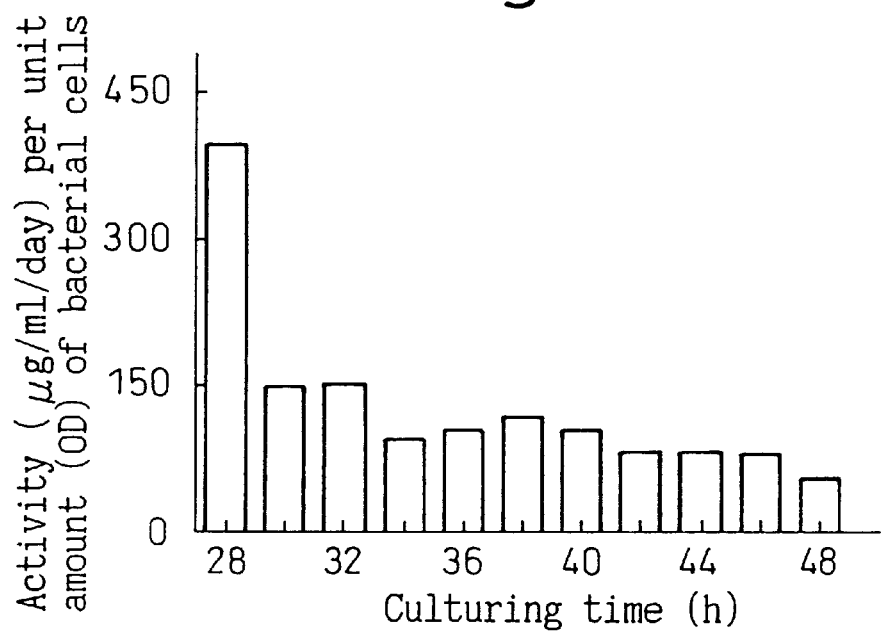
FIG. 10 is a graph which shows the specific decomposition efficiency of trichloroethylerie per bacterial cells (OD= 1.0) when the bacterium was cultured for various times in the time course of culture as set forth in FIG. 9.
Figure 11:
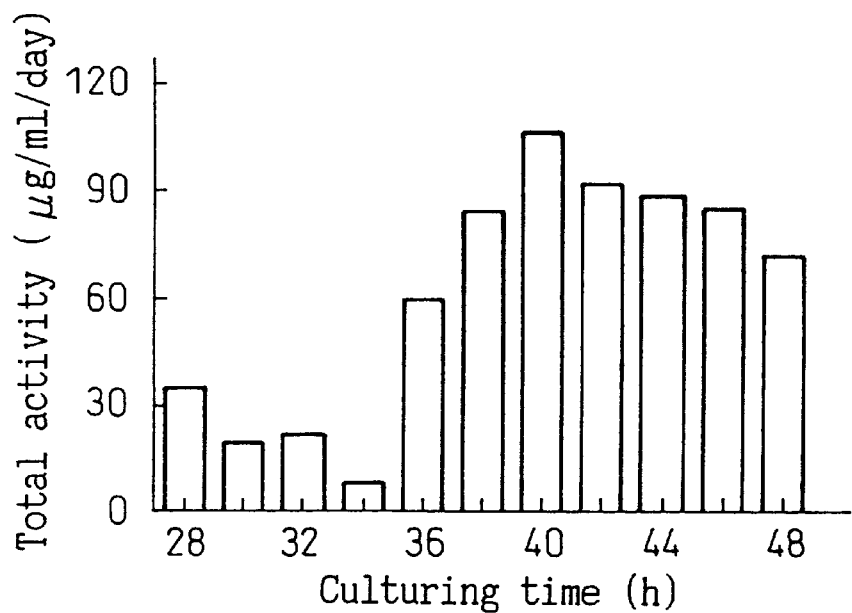
FIG. 11 is a graph which shows the decomposition efficiency of trichloroethylene per total bacterial cells when the bacterium was cultured for various times in the time course of culture as set forth in FIG. 9.

The suspension of the bacterial mass was dispensed in a 20 ml vial and trichloroethylene was added thereto in such an amount that it became 30 ppm when all the ingredients were dissolved in the liquid phase. The vial was plugged with a Teflon-coated butyl rubber septum and sealed with an aluminum cap. After culturing at 30° C. under shaking for 24 hours, the gas phase in the vial was analyzed by a gaschromatograph equipped with an ECD detector. The results are shown in FIG. 9 to FIG. 11. The line graphs in FIG. 9 represent turbidity of the culture liquid and phenol concentration. The bar graphs in FIG. 10 represent the decomposition activity per unit amount of the bacterial mass (specific activity) of the microorganism of the present invention harvested at respective time of culturing. The bar graphs in FIG. 11 represent the decomposition activity per unit amount of the culture liquid (the total activity) of the microorganism of the present invention which was harvested at respective time of culturing.

From the results obtained as above on the activity of trichloroethylene decomposition, the specific activity notably increases from the induction phase to the logarithmic growth phase, leveling off thereafter at a certain level. But it gradually decreased after the residual phenol became zero. However, the total activity remained at the highest value at the stationary phase when phenol concentration became around zero. These observations have shown that a bacterial mass having a high activity of trichloroethylene decomposition can be obtained by culturing while monitoring the turbidity of culture liquid and phenol concentration prior to inoculation into the soil, and terminating the culture at the timing that the increase in turbidity ceases to enter the stationary phase and phenol concentration becomes almost zero.

Example 8

The microorganism of the present invention was cultured in a manner similar to Example 7 and turbidity of the culture liquid and phenol concentration were measured in a manner similar to Example 6. Furthermore, when the phenol concentration reached zero in the middle of culturing 500 ppm of phenol was added again and culture was continued. The bacterial mass in the culture was harvested by centrifuging at 5000 r.p.m. for 10 minutes and then resuspended into the NMS medium having an amount equal to that of the culture medium.

The $OD_{600}$ of the suspension was 0.2 (then cell count was $2.5 \times 10^8$ c.f.u./ml). The suspension of the bacterial mass was dispensed in a 20 ml vial and trichloroethylene was added thereto in such an amount that it became 30 ppm when all the ingredients were dissolved in the liquid phase. The vial was plugged with a Teflon-coated butyl rubber stopper and sealed with an aluminum cap. After culturing at 30° C. under shaking for 24 hours, the gas phase in the vial was analyzed by a gaschromatograph equipped with an ECD detector.

Figure 12:
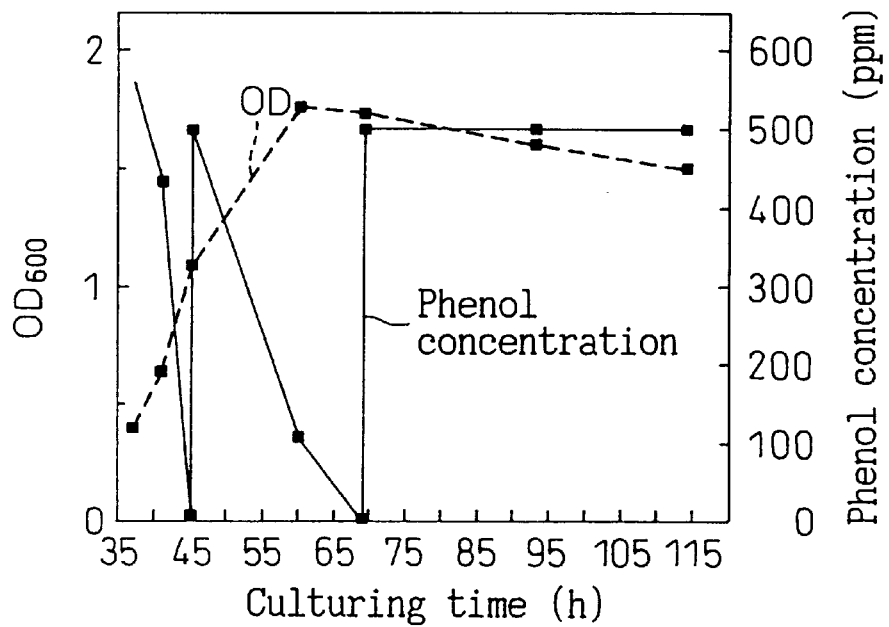
FIG. 12 is a graph which shows growth curve (OD) and a time course of phenol consumption when strain MO7 of the present invention was cultured in a medium containing phenol (500 ppm) and then further cultured by adding phenol when phenol was consumed completely.
Figure 13:
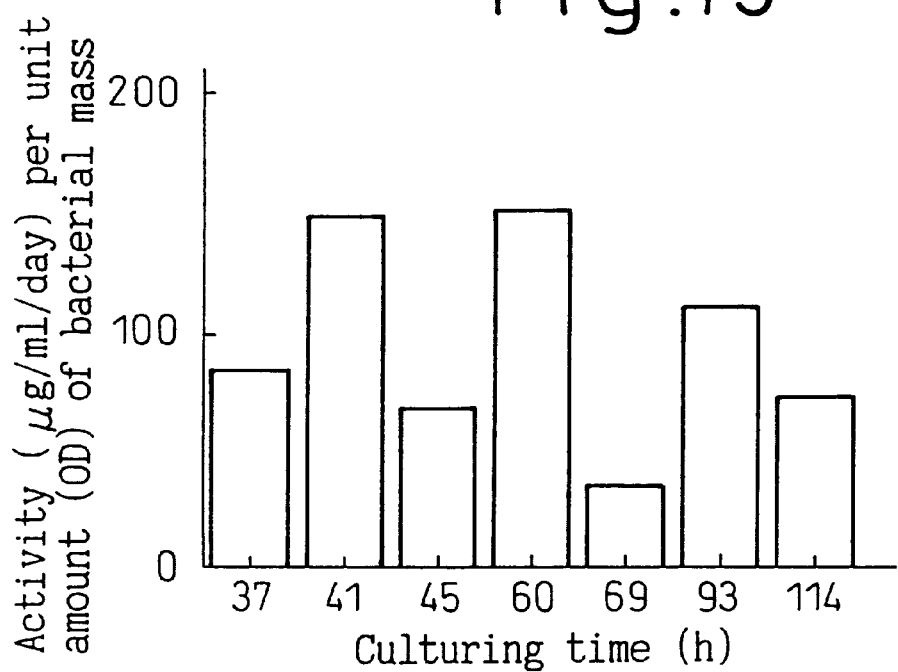
FIG. 13 is a graph which shows the specific decomposition efficiency of trichloroethylene per bacterial cells (OD= 1.0) when the bacterium was cultured for various times in the time course of culture as set forth in FIG. 12.
Figure 14:
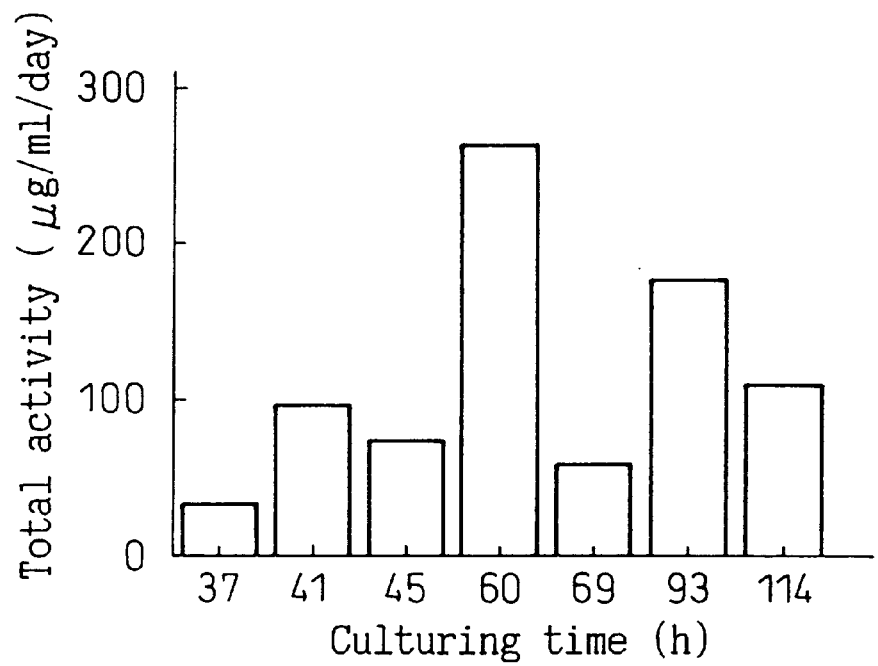
FIG. 14 is a graph which shows the decomposition efficiency of trichloroethylene per total bacterial cells when the bacterium was cultured to various times in the time course of culture of FIG. 12.

The results are shown in FIG. 12 to FIG. 14. The line graphs in FIG. 12 represent turbidity of the culture liquid and phenol concentration at the stage of culturing prior to harvesting. The bar graphs in FIG. 13 represent the specific activity of the microorganism of the present invention which was harvested at respective time of culturing. The bar graphs in FIG. 14 represent the total activity of the microorganism of the present invention which was harvested at respective time of culturing. When 500 ppm of phenol was added to the culture liquid at 45 hours of culturing when the residual phenol became almost zero, the phenol concentration decreased again and the turbidity of the culture liquid increased. Therefore, phenol was added again at 69 hours, but neither increase in turbidity of the culture liquid nor decrease in phenol concentration were observed.

With regard to the activity of trichloroethylene decomposition, high specific activities were obtained when sufficient phenol is remaining at around the stationary phase during 41 hours to 60 hours as shown in FIG. 13, but the specific activity decreased thereafter when phenol concentration decreased. When phenol was added at 93 hours, both the amount of the bacterial mass and the specific activity decreased. However, during the period from 93 hours to 114 hours when there was residual phenol, the specific activity was higher than during 45 hours to 69 hours when most of the phenol was decomposed. On the other hand, the total activity was the highest at 60 hours when both of the amount of the bacterial mass and specific activity were high, providing the total activity 2.5 times higher than when phenol is added only at the start of culturing.

Next, trichloroethylene decomposition in the soil will be explained with reference to the following examples.

Example 9

To a 100 ml vial was added 30 g of sandy soil (air-dried) which was artificially contaminated with trichloroethylene. The microorganism of the present invention was cultured under shaking at 30° C. for 3 days in 1.5 ml, 4.5 ml, 7.5 ml, 15 ml, or 30 ml of the NMS medium which had 500 ppm of phenol and 0.05% yeast extract added thereto, and then was centrifuged to harvest the cells, which were resuspended into an appropriate amount of the NMS medium so that the water content in the soil became 25% after addition of the suspension of the bacterial mass. After adding the suspension (containing no phenol) of the bacterial mass to the soil, the vial was sealed with a Teflon-coated rubber septum and sealed with an aluminium cap, and then allowed to stand at 30° C. for a certain period of time.

Figure 15:
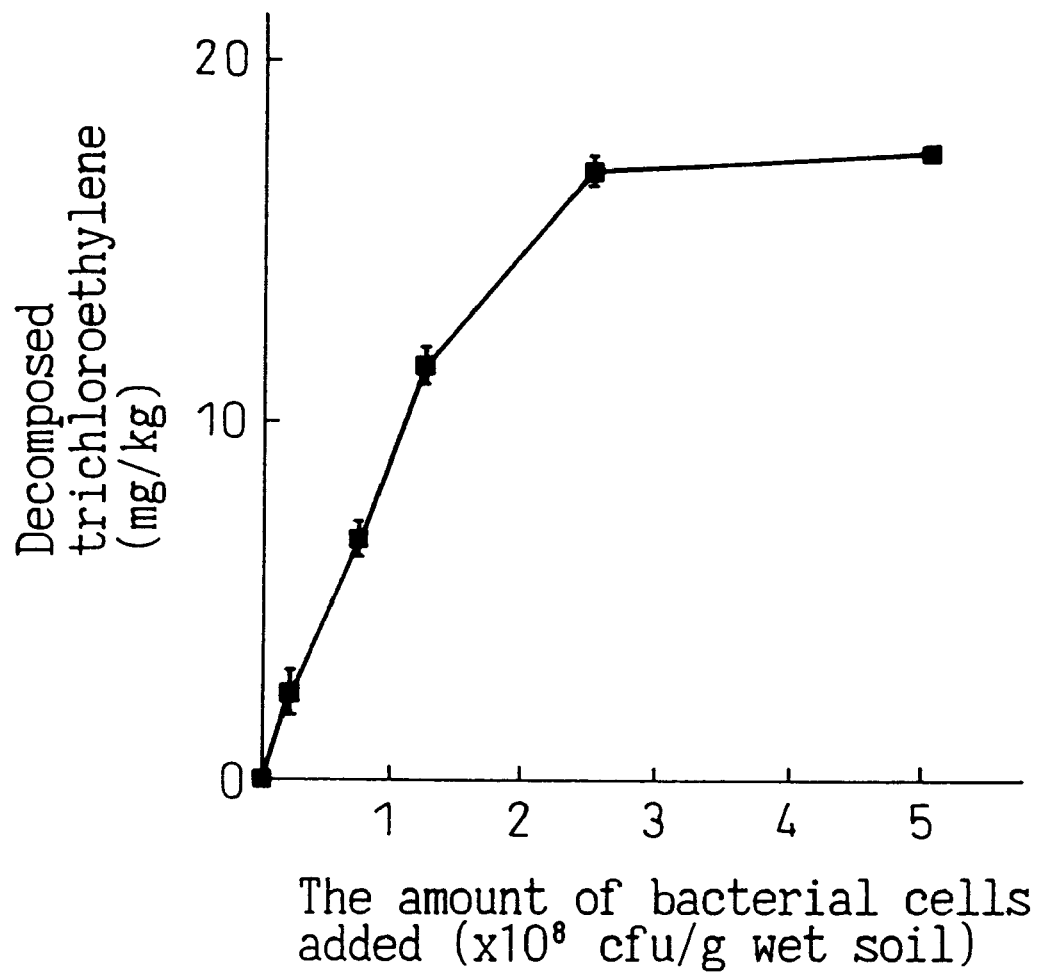
FIG. 15 is a graph which shows the relationship between the amount of the bacterial cells and the amount of trichloroethylene decomposed when trichloroethylene was decomposed by adding the cultured bacterial cells of strain MO7 of the present invention into the soil containing trichloroethylene.

Thereafter, to a vial containing 30 g of the soil were added 50 ml of deionized water aerated with the air which had been passed through activated charcoal and 10 ml of n-hexane, and then the vial was sealed. The vial was sonicated in the sonicating washer for 10 minutes and then was shaken in a shaker for 10 minutes. The separated n-hexane was analyzed using a gaschromatograph equipped with an ECD detector. The result as shown in FIG. 15 indicated that trichloroethylene decomposition and the density of the bacterial mass correlated until the density of the bacterial mass reached $2.5 \times 10^8$ cfu/g wet soil (15 ml of the culture liquid), but it became saturated at about $5 \times 10^8$ cfu/g wet soil (30 ml of the culture liquid) or higher. Therefore, it was revealed that when the microorganism of the present invention is used to decompose trichloroethylene the density of the bacterial mass of about $2.5 \times 10^8$ cfu/g wet soil is most suitable and that the microorganism of the present invention has a characteristics which enables an estimation of a minimum amount of bacterial mass required for purification of a given concentration of a contaminant in the soil.

Example 10

To a 100 ml vial was added 30 g of sandy soil (air-dried) which was artificially contaminated with trichloroethylene. The microorganism of the present invention was cultured under shaking at 30" C. for 3 days in 7.5 ml of the NMS medium which had 500 ppm of phenol and 0.05% yeast extract added thereto, and then was centrifuged to harvest the cells, which were then resuspended into an appropriate amount of the NMS medium so that the water content in the soil became 25% after addition of the suspension of the bacterial mass. After adding the suspension (containing no phenol) of the bacterial mass to the soil, the vial was sealed with a Teflon-coated rubber septum and sealed with an aluminium cap, and then allowed to stand at 30° C. for a certain period of time.

Thereafter, to a vial containing 30 g of the soil were added 50 ml of deionized water aerated with the air which had been passed through activated charcoal and 10 ml of n-hexane, and the vial was sealed. The vial was sonicated in the sonicating washer for 10 minutes and then was shaken in a shaker for 10 minutes. The separated n-hexane was analyzed using a gaschromatograph equipped with an ECD detector. The result as shown in FIG. 16 indicates that when the bacterial mass corresponding to 7.5 ml of the culture liquid was added twice to the soil, the efficiency of decomposition was equal to when the bacterial mass corresponding to 15 ml of the culture liquid was added at one addition.

It is difficult to supply at one addition the amount of culture liquid necessary to decompose trichloroethylene contained in the contaminated soil in terms of the actual amount needed (the actual amount of the contaminated soil is more than a few dozen $m^3$), and the decomposing microorganism must be sequentially cultured and added to the soil. It was revealed that sequential addition of the microorganism of the present invention gives the same effect as that obtained when the required bacterial mass is added at one addition. Therefore, by adding a small amount of the culture liquid repeatedly the microorganism of the present invention can deal with a vast area of the contaminated site for which one-time culture and infusion of the bacterial mass is insufficient.

Example 11

To a 100 ml vial was added 30 g of sand grain soil (air-dried) which was artificially contaminated with trichloroethylene at the desired concentrations. The concentration of the contaminant in the soil was set at 15, 30, 45, 100, and 150 mg/kg. The microorganism of the present invention was cultured under shaking at 30° C. for 3 days in 15, 30, and 45 ml of the NMS medium which had 500 ppm of phenol and 0.05% yeast extract added thereto, and then was centrifuged to harvest the cells, which were resuspended into an appropriate amount of the NMS medium so that the water content in the soil became 25% after addition of the suspension of the bacterial mass. After adding the suspension (containing no phenol) of the bacterial mass to the soil, the vial was sealed with a Teflon-coated rubber septum and sealed with an aluminium cap, and then allowed to stand at 30° C. for a certain period of time. The density of the bacterial mass in the soil $9.4 \times 10^8$, $1.9 \times 10^9$, and $2.8 \times 10^9$ cfu/cg wet soil for 15, 30, and 45 ml of the culture liquid, respectively.

Figure 17:
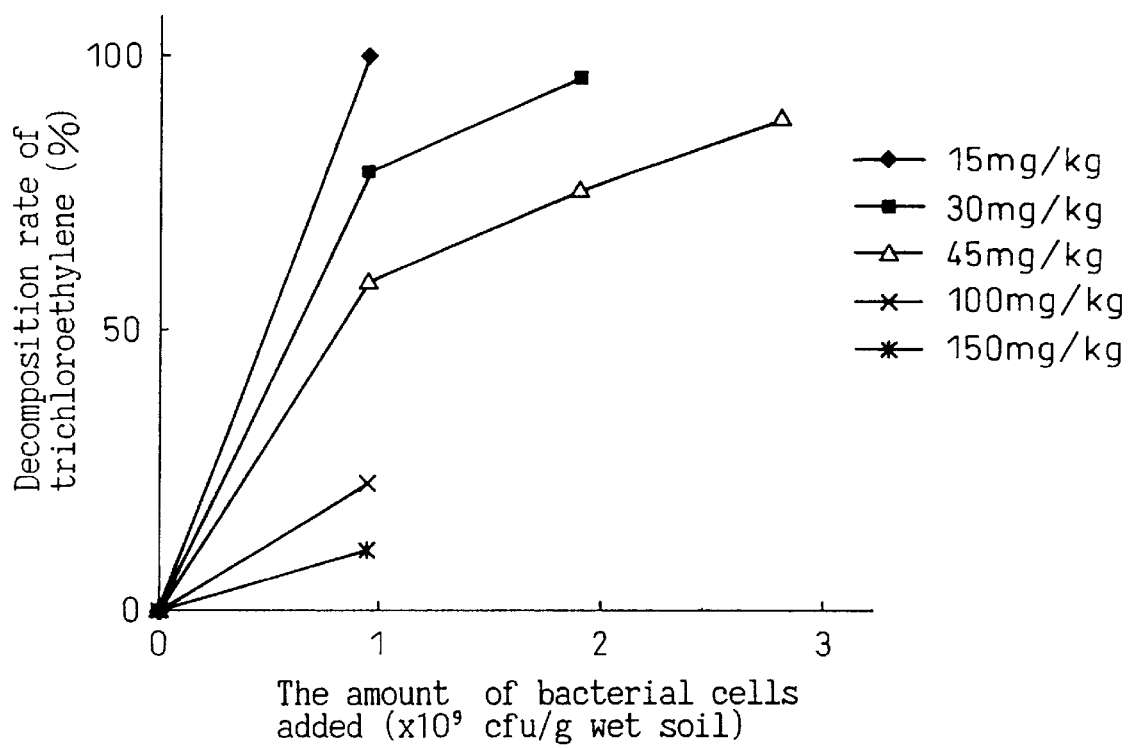
FIG. 17 is a graph which shows the relationship between the amount of the inoculated bacterial cells and the decomposition efficiency of trichloroetbylene at various initial concentration of trichloroethylene in soil when trichloroethylene was decomposed by adding the cultured bacterial mass of strain MO7 of the present invention.

Thereafter, to a vial containing 30 g of the soil were added 50 ml of deionized water aerated with the air which had been passed through activated charcoal and 10 ml of n-hexane, and then the vial was sealed. The vial was sonicated in the sonicating washer for 10 minutes and then was shaken in a shaker for 10 minutes. The separated n-hexane was analyzed using a gaschromatograph equipped with an ECD detector. The result as shown in FIG. 17 indicates that a very high concentration (about 150 mg/kg) of trichloroethylene in the soil could be decomposed. The above result indicated that purification of a high concentration (about 150 mg/kg) contaminant can be effected by increasing the amount of the bacterial mass added or by sequential addition because the amount of trichloroethylene decomposed increases in proportion to the amount of the bacterial mass added to the soil.

Example 12

To a 100 ml vial which can be sealed with a Teflon-coated rubber septum was added 30 g of sandy soil (air-dried) which was artificially contaminated with trichloroethylene. The microorganism of the present invention was cultured under shaking at 30° C. for 3 days in the NMS medium which had 500 ppm of phenol and 0.05% yeast extract added thereto, and then was centrifuged to harvest the cells, which were resuspended into an appropriate amount of the NMS medium so that the water content in the soil became 25% and the inoculated amount of bacterial mass became $10^8$ to $10^9$ cells/g wet soil after addition of the suspension of the bacterial mass. After adding the suspension (containing no phenol) of the bacterial mass to the soil, the vial was sealed with a Teflon-coated rubber stopper, and then allowed to stand at 30° C. for a certain period of time.

Thereafter, to a vial containing 30 g of the soil were added 50 ml of deionized water aerated with the air which was passed through activated charcoal and 10 ml of n-hexane, and the vial was sealed. The vial was sonicated in the sonicating washer for 10 minutes and then was shaken in a shaker for 10 minutes. The separated n-hexane was analyzed using a gaschromatograph equipped with an ECD detector. Time course of changes in trichloroethylene concentration in the soil was determined by preparing a multiple of samples at the same time and extracting the entire volume of a part of samples after passage of a given time, followed by measurement. They were stored at 4° C. until extraction.

The measurement of trichloroethylene concentration in the soil was also conducted using a method indicated in the Environmental Standard (the Soil Environmental Standard) related to the contamination of the soil. Thus, the soil sample and the solvent (hydrochloric acid was added to purified water and pH was adjusted to 5.8 to 6.3) were added at a weight to volume ratio of 10% to an Erlenmeyer flask with a screw socket having a stirrer bar, and then the flask was immediately sealed. At this time, care was taken to make the volume of the mixture be not less than 500 ml and to minimize the head space in the Erlenmeyer flask with a screw socket relative to the volume of the mixture. The prepared sample liquid was stirred continuously for 4 hours with the magnetic bar keeping the liquid at ordinary temperature and ordinary pressure.

Figure 18:
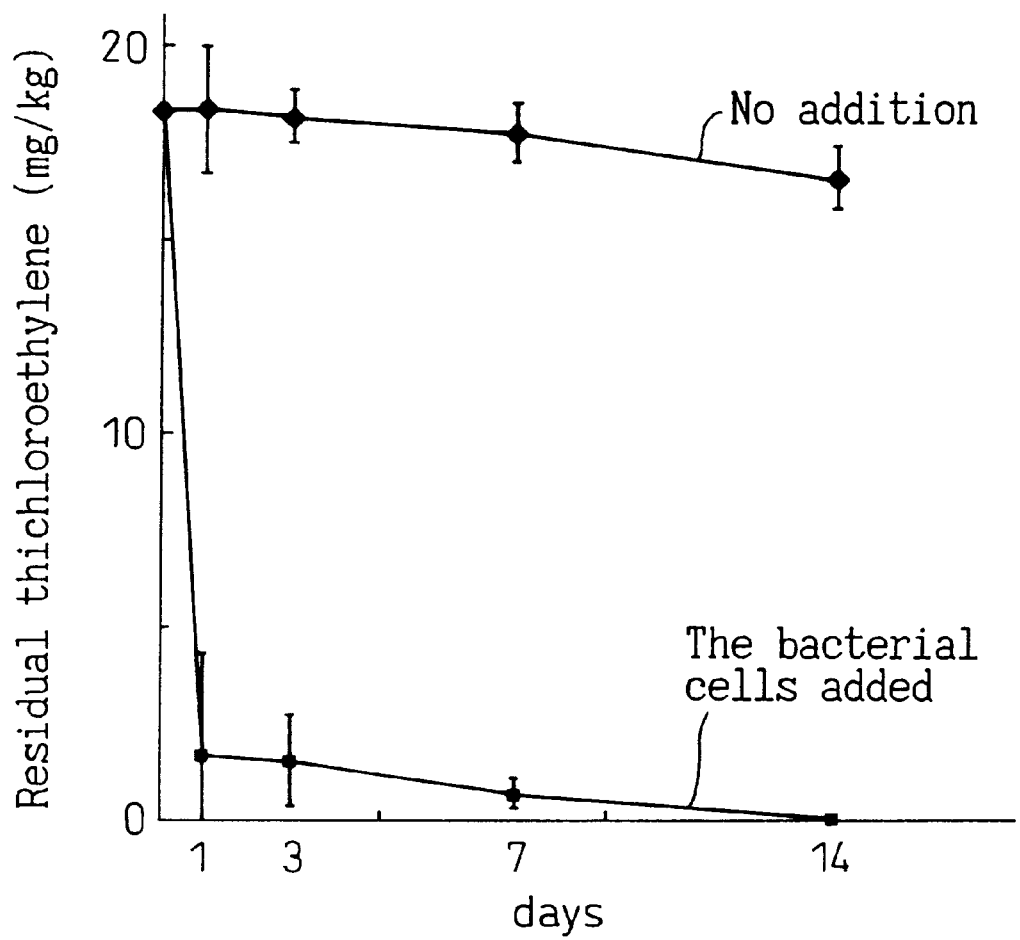
FIG. 18 is a graph which shows a time course of the residual trichloroethylene in soil when trichloroethylene was decomposed by adding the cultured bacterial cells of strain MO7 of the present invention to the soil containing trichloroethylene.

After the sample liquid was allowed to stand for 30 minutes, it was aspirated into a glass syringe. A filter holder fitted with a membrane filter having a pore size of $0.45\mu$ was connected to the syringe and tine plunger was pressed to exclude the air and the initial few ml of the liquid, and then the filtrate was collected in fractions into stoppered test tubes, from which an amount necessary for determination was weighed out and was subjected to analysis by gaschromatography. The result as shown in FIG. 18 indicated that 90% of the total trichloroethylene in the soil was decomposed in a day after addition of the bacterial mass.

It was revealed therefore that the method of purifying trichloroethylene by adding the microorganism of the present invention into the soil is a technology which has a high purification ability almost equal to decomposition capacity of about 18 mg/kg of trichloroethylene in the soil in a day. When the soil sample at 7 days of standing was measured according to an analytical method designated by the nation (the Environmental Standard, the Soil Environmental Standard related to the contamination of the soil), the concentration of trichloroethylene was below the base value (0.03 ppm). As a result, it was revealed that trichloroethylene can be purified to the level which satisfies the environmental standard by purifying the contaminated soil using the microorganism of the present invention. It is generally accepted that the physical means of treatment such as vacuum extraction is unable to purify from low concentrations, but the use of the microorganism of the present invention enables purification to the level lower than the base value.

Example 13

To a 100 ml vial which can be sealed with a Teflon-coated rubber septum was added 30 g of sandy soil (air-dried) which was artificially contaminated with trichloroethylene. The microorganism of the present invention was cultured under shaking at 30° C. for 3 days in the NMS medium which had 500 ppm of phenol and 0.05% yeast extract added thereto, and then was centrifuged to harvest the cells, which were resuspended into an appropriate amount of the NMS medium so that the water content in the soil became 25% and the inoculated amount of bacterial mass became $10^8$ to $10^9$ cells/g wet soil after addition of the suspension of the bacterial mass. After adding the suspension (containing no phenol) of the bacterial mass to the soil, the vial was sealed with a Teflon-coated rubber stopper, and then allowed to stand at 30° C. for a certain period of time. Thereafter, analysis was conducted on byproducts which are said to be formed in association with trichloroethylene decomposition in the soil.

Figure 20:
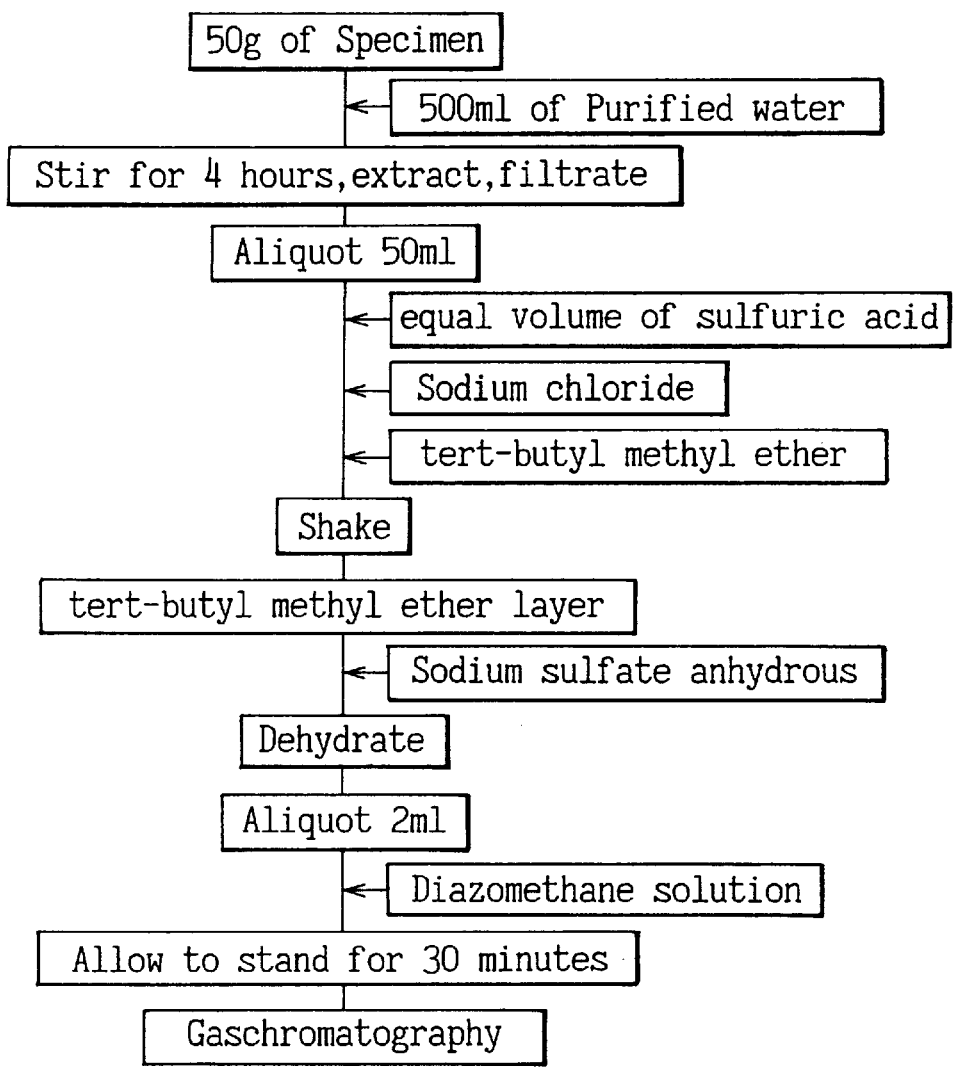
FIG. 20 shows a flow chart of the analytical method of dichloroacetate and trichloroacetate.
Figure 21:
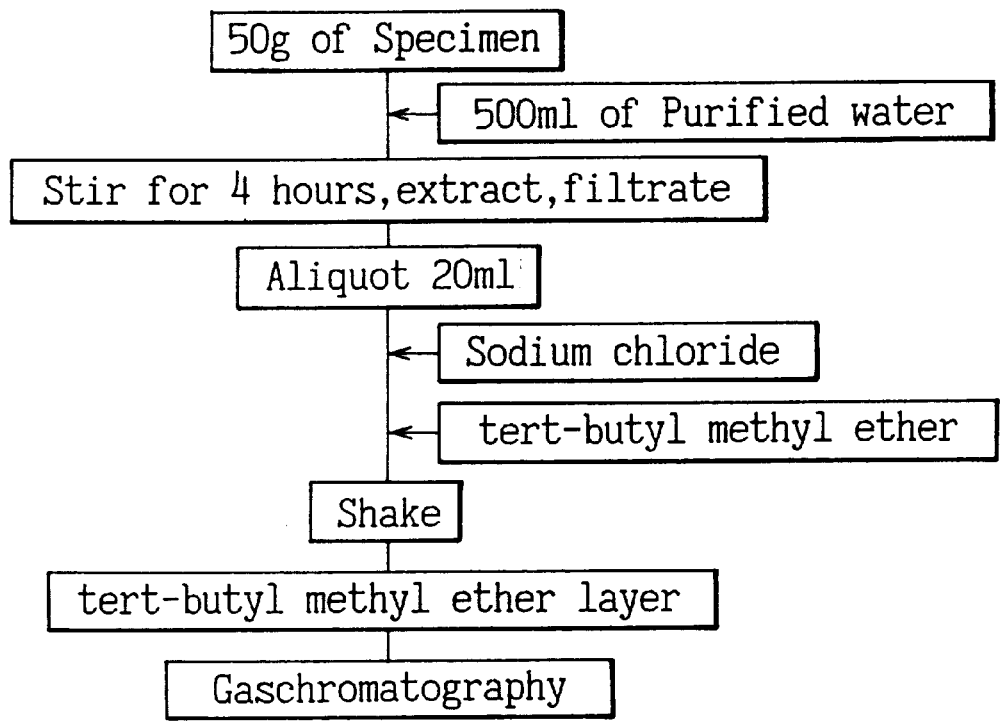
FIG. 21 is shows a flow chart of the analytical method of trichloroethanol.
Figure 22:
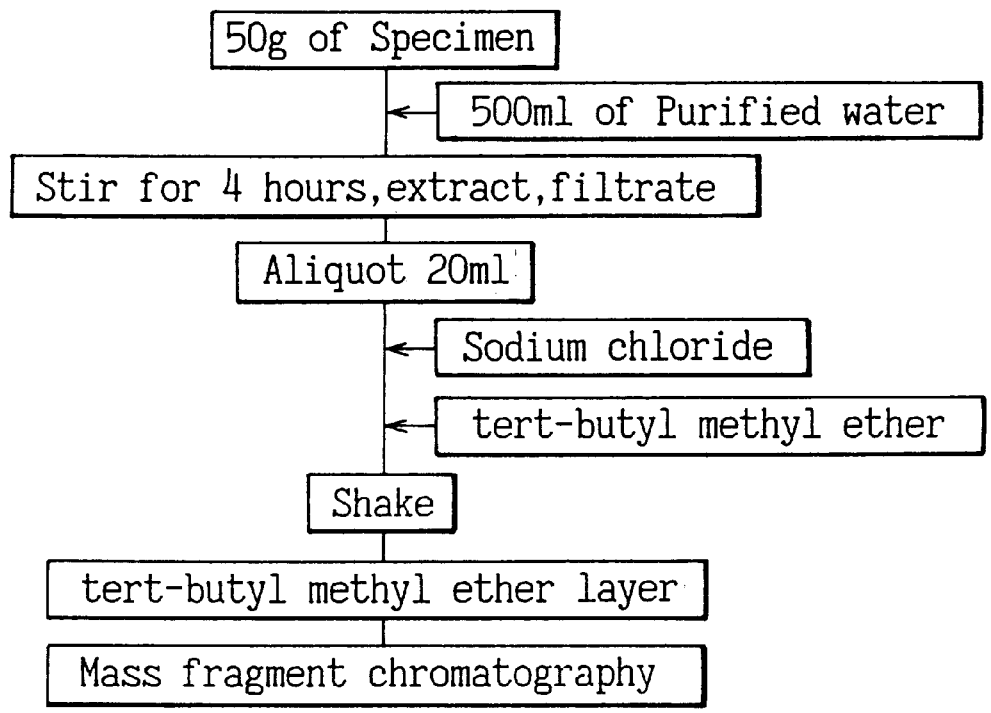
FIG. 22 is shows a flow chart of the analytical method of hydrated chloral.

The byproducts in the soil were analyzed as follows: vinyl chloride, 1,1-dichloroethylene, cis-1,2-dichloroethylene, and trans-1,2-dichloroethylene were analyzed in the method shown in FIG. 19. Dichloro acetate and trichloro acetate, trichloroethanol, and hydrated chloral were analyzed in the method shown in FIGS. 20, 21, and 22, respectively. The result as shown in Table 9 indicated that all byproducts were below the detection limit.

The dechlorination reaction of trichloroethylene under an anaerobic condition leads to accumulation of dichloroethylenes which is more toxic. It is also known that the decomposition process under an aerobic condition starting with formation of trichloroethylene oxide produces dichloro acetate etc. as intermediate products. There was no accumulation of harmful substances on decomposition of trichloroethylene by the microorganism of the present invention in the soil. Although the presence of substances other than those measured is unknown, this technology appeared to be a highly safe method.

TABLE 8

| Item to be analyzed | Result | Detection limit |
| --- | --- | --- |
| Vinyl chloride | Not detected | 0.01 ppm |
| 1,1-dichloroethylene | Not detected | 0.01 ppm |
| cis-1,2-dichloroethylene | Not detected | 0.01 ppm |
| trans-1,2-dichloroethylene | Not detected | 0.01 ppm |
| Dichloroacetate | Not detected | 0.05 ppm |
| Trichloroethanol | Not detected | 0.01 ppm |
| Trichloroacetate | Not detected | 0.05 ppm |
| Hydrated chloral | Not detected | 0.05 ppm |

Example 14

To a 100 ml vial which can be sealed with a Teflon-coated rubber septum was added 30 g of sandy soil (air-dried) which was artificially contaminated with trichloroethylene. The microorganism of the present invention was cultured under shaking at 30° C. for 3 days in the NMS medium which had 500 ppm of phenol and 0.05% yeast extract added thereto, and then was centrifuged to harvest the cells, which were resuspended into an appropriate amount of the NMS medium so that the water content in the soil became 25% and the inoculated amount of bacterial mass became $10^8$ to $10^9$ cells/g wet soil after addition of the suspension of the bacterial mass. After plating the suspension of the bacterial mass onto a petri dish to a thickness of about 1 mm, it was sterilized under irradiation of a 15 W Ultra violet lamp with a wavelength of 260 nm for not less than 60 seconds at a distance of 40 cm from the light source. After adding the suspension (containing no phenol) of the microorganism of the present invention into the soil, the vial was sealed with a Teflon-coated rubber stopper, and then allowed to stand at 30° C. for a certain period of time.

Figure 23:
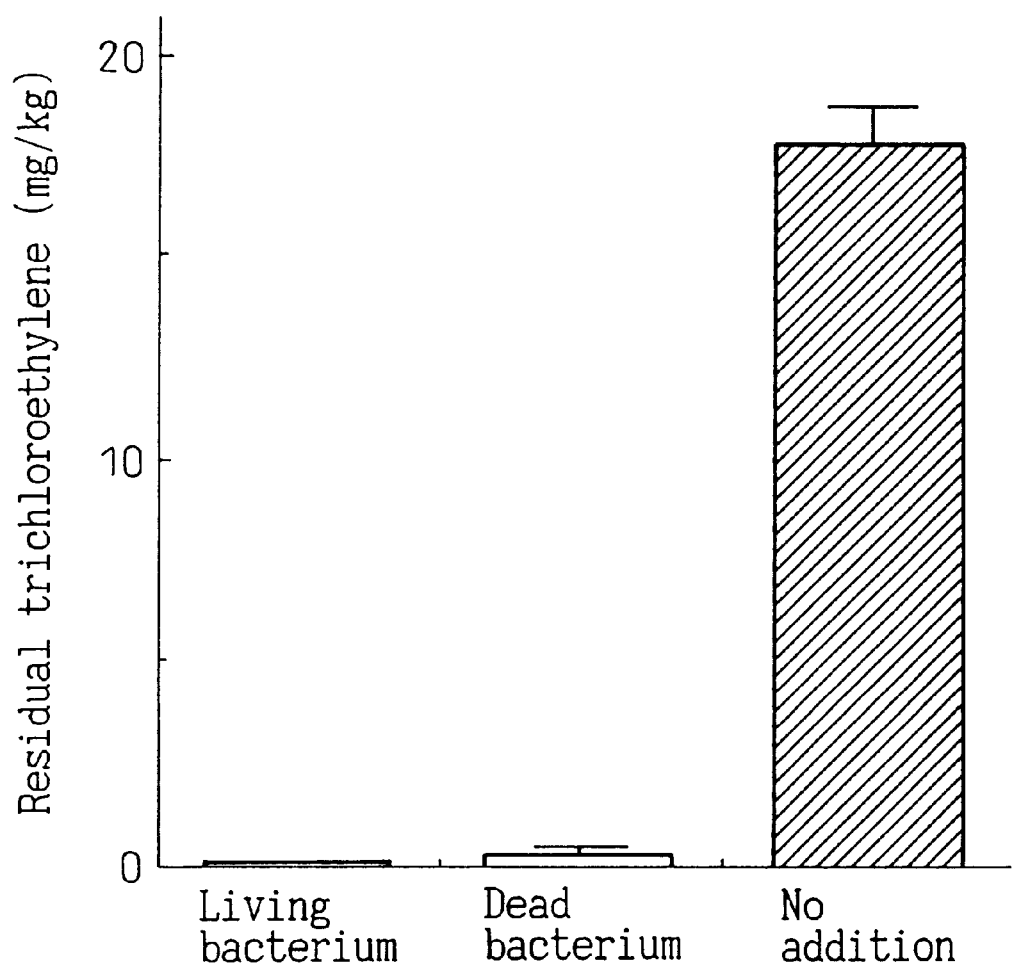
FIG. 23 is a graph which shows a result when trichloroethylene was decomposed by adding the cultured bacterial cells of strain MO7 of the present invention or the sterilized product thereof to the soil containing trichloroethylene.

Thereafter, to a vial containing 30 g of the soil were added 50 ml of deionized water aerated with the air which had been passed through activated charcoal and 10 ml of n-hexane, and then the vial was sealed. The vial was sonicated in the sonicating washer for 10 minutes and then was shaken in a shaker for 10 minutes. The separated n-hexane was analyzed using a gaschromatograph equipped with an ECD detector. Furthermore, in an experiment in which the suspension of sterilized bacterial mass at an amount of 1/100 of that of the NYG medium was inoculated or the suspension was plated as it was onto the NYG agar medium and cultured at 30° C., neither increase in turbidity of the culture liquid nor colony formation were observed, and thereby it was confirmed that there was complete sterilization. The result as shown in FIG. 23 indicated that the dead cells and living cells gave an equal degree of decomposition of trichloroethylene.

Although most of the purification methods using microorganisms comprise adding living organisms into the soil, addition of the bacterial mass into the soil is currently difficult from a viewpoint of public acceptance. It is also being feared that it has a potential risk of producing a far-reaching effect on the ecological system by releasing a specific microorganism into the environment. But the addition of the microorganism which has completely lost the propagating activity by sterilization treatment is equivalent to that of mere organic materials, and thus is believed to have little effect on the ecological system. Therefore an experiment was conducted in which addition of the decomposing microorganism sterilized with ultraviolet irradiation into the soil was investigated. The result indicated that the addition of the dead bacterial mass proved to be an extremely useful method.

The invention disclosed in Japanese Unexamined Patent Publication No. 8(1996)-3012 claims that the effect on the ecological system can be minimized by crushing the decomposing bacteria and then spraying it to the soil. But, it is readily anticipated that the spraying of a large mass of decomposing bacterium to the contaminated soil is in fact difficult because crushing of microorganisms takes extensive equipment, a lot of time and labor. The known enzymes which have trichloroethylene-oxidizing activity require NAD as a coenzyme. But because the coenzyme is very expensive, it would be extremely difficult to supply the coenzyme in the concentration necessary for the decomposition reaction of the enzyme which was released by crushing the bacterium from the bacterial mass. On the other hand, the method using the microorganism of the present invention has no such problems, and enables purification of trichloroethylene etc. at low cost and with minimum effects on the ecological system.

Example 15

To a 100 ml vial which can be sealed with a Teflon-coated rubber septum was added 30 g of sand grain soil (air-dried) which was artificially contaminated with trichloroethylene. The microorganism of the present invention was cultured under shaking at 30° C. for 3 days in the NMS medium which had 500 ppm of phenol and 0.05% yeast extract added thereto, and then was centrifuged to harvest the cells, which were resuspended into an appropriate amount of the NMS medium so that the water content in the soil became 25% and the inoculated amount of bacterial mass became $10^8$ to $10^9$ cells/g wet soil after addition of the suspension of the bacterial mass. After plating the suspension of the bacterial mass onto a petri dish to a thickness of about 1 mm, and then sterilized under irradiation of a 15 W ultra violet lamp with a wavelength of 260 nm for not less than 60 seconds at a distance of 40 cm from the light source.

After adding the suspension (containing no phenol) of the sterilized microorganism of the present invention into the soil, the vial was sealed with a Teflon-coated rubber stopper, and then allowed to stand at 30° C. for a certain period of time. After that, trichloroethylene in the soil was allowed to be decomposed and the byproducts which is believed to be formed in association with trichloroethylene decomposition were analyzed in a similar manner to Example 13. Furthermore, in an experiment in which the suspension of sterilized bacterial mass at an amount of 1/100 of that of the NYG medium was inoculated or the suspension was plated as it was onto the NYG agar medium and cultured at 30° C., neither increase in turbidity of the culture liquid nor colony formation were observed, and thereby it was confirmed that there was complete sterilization.

The result as shown in Table 10 indicated that all byproducts were below the detection limit. The dechlorination reaction of trichloroethylene under an anaerobic condition leads to accumulation of dichloroethylenes which is more toxic. It is also known that the decomposition process under an aerobic condition which starts with formation of trichloroethylene oxide produces dichloroacetate etc. as intermediate products. There was no accumulation of harmful substances on decomposition of trichloroethylene by the microorganism of the present invention in the soil. Although the presence of substances other than those measured is unknown, it was suggested that this technology is a highly safe method.

TABLE 9

| Item to be analyzed | Result | Detection limit |
|---|---|---|
| Vinyl chloride | Not detected | 0.01 ppm |
| 1,1-dichloroethylene | Not detected | 0.01 ppm |
| cis-1,2-dichloroethylene | Not detected | 0.01 ppm |
| trans-1,2-dichloroethylene | Not detected | 0.01 ppm |
| Dichloroacetate | Not detected | 0.05 ppm |
| Trichloroethanol | Not detected | 0.01 ppm |
| Trichloroacetate | Not detected | 0.05 ppm |
| Hydrated chloral | Not detected | 0.05 ppm |

Example 16

To a 100 ml vial which can be sealed with a Teflon-coated rubber septum was added 30 g of sandy soil (air-dried) which was artificially contaminated with trichloroethylene. The microorganism of the present invention was cultured under shaking at 30° C. for 3 days in the NMS medium which had 500 ppm of phenol and 0.05% yeast extract added thereto, and then was centrifuged to harvest the cells, which were resuspended into an appropriate amount of the NMS medium so that the water content in the soil became 25% and the inoculated amount of bacterial mass was $10^8$ to $10^9$ cells/g wet soil after addition of the suspension of the bacterial mass. After adding the suspension (containing no phenol) of the microorganism of the present invention into the soil, the vial was sealed with a Teflon-coated rubber stopper, and then allowed to stand at 20° C. for a certain period of time.

Thereafter, to a vial containing 30 g of the soil were added 50 ml of deionized water aerated with the air which had been passed through activated charcoal and 10 ml of n-hexane, and the vial was sealed. The vial was sonicated in the sonicating washer for 10 minutes and then was shaken in a shaker for 10 minutes. The separated n-hexane was analyzed using a gaschromatograph equipped with an ECD detector.

Figure 24:
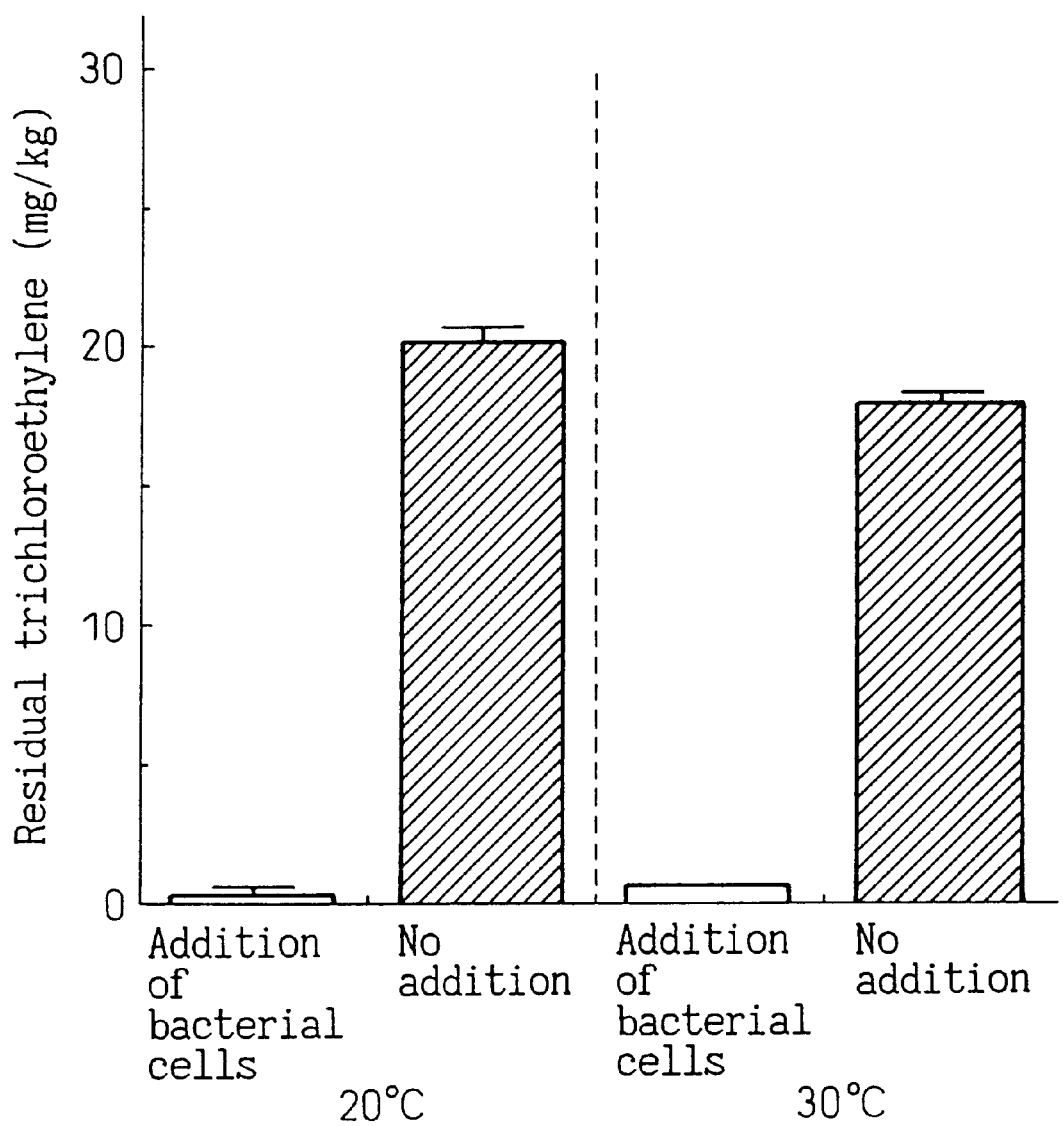
FIG. 24 is a graph which shows the effect of temperature (20° C., 30° C.) on the decomposition efficiency of trichloroethylene when trichloroethylene was decomposed by adding the cultured bacterial cells of strain MO7 of the present invention to the soil containing trichloroethylene.

The result as shown in FIG. 24 indicated that trichloroethylene was decomposed at 20° C. to a degree equivalent to that at 30° C. Since it was suggested that trichloroethylene is sufficiently decomposed at the temperature of the soil, the microorganism of the present invention proved to have a high practical utility as compared to the others.

Example 17

To a 100 ml vial was added 30 g of sand grain soil (air-dried) which was artificially contaminated with trichloroethylene. The microorganism of the present invention was cultured under shaking at 30° C. for 1 day in the NMS medium which had 500 ppm of phenol and 0.05% yeast extract added thereto. The culture liquid at a volume of 1/100 of that of the NMS medium (or the PH medium) containing 500 ppm, 0.02%, and 1 mM of phenol, yeast extract, and glucose, respectively in the soil was added and then added to the soil. The density of the bacterial mass was set at $10^6$ cells/g wet soil, and the water content set at 25% at the time of culture liquid addition.

The vial was sealed with a Teflon-coated rubber septum, and then allowed to stand at 30° C. for a certain period of time. Thereafter, to a vial containing 30 g of the soil were added 50 ml of deionized water aerated with the air which had been passed through activated charcoal and 10 ml of n-hexane, and then the vial was sealed. The vial was sonicated in the sonicating washer for 10 minutes and then was shaken in a shaker for 10 minutes. The separated n-hexane was analyzed using a gaschromatograph equipped with an ECD detector.

Figure 25:
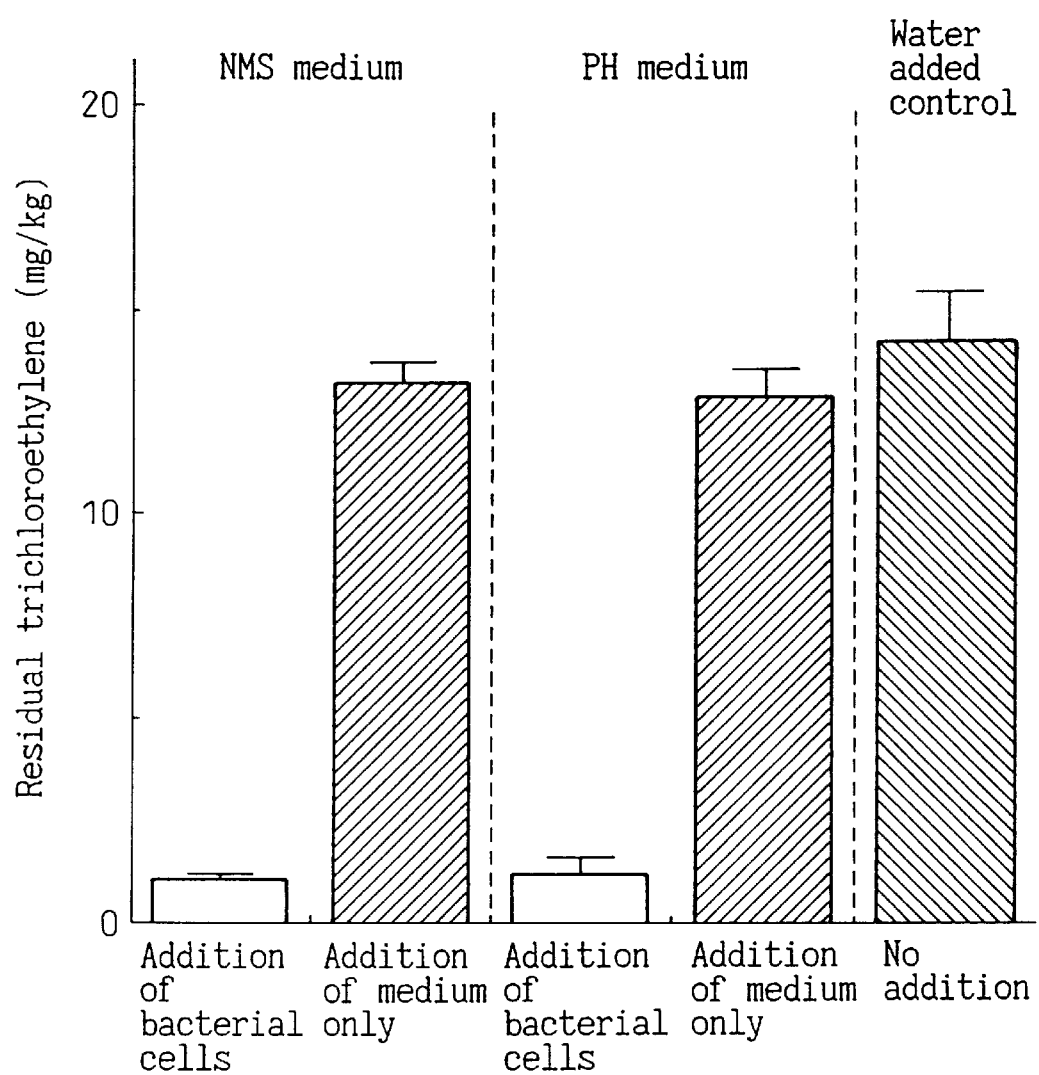
FIG. 25 is a graph which shows a result when trichloroethylene was decomposed by adding a small amount of the cultured bacterial cells of strain MO7 of the present invention and adding an inducer (phenol) to the soil containing trichloroethylene.
Figure 26:
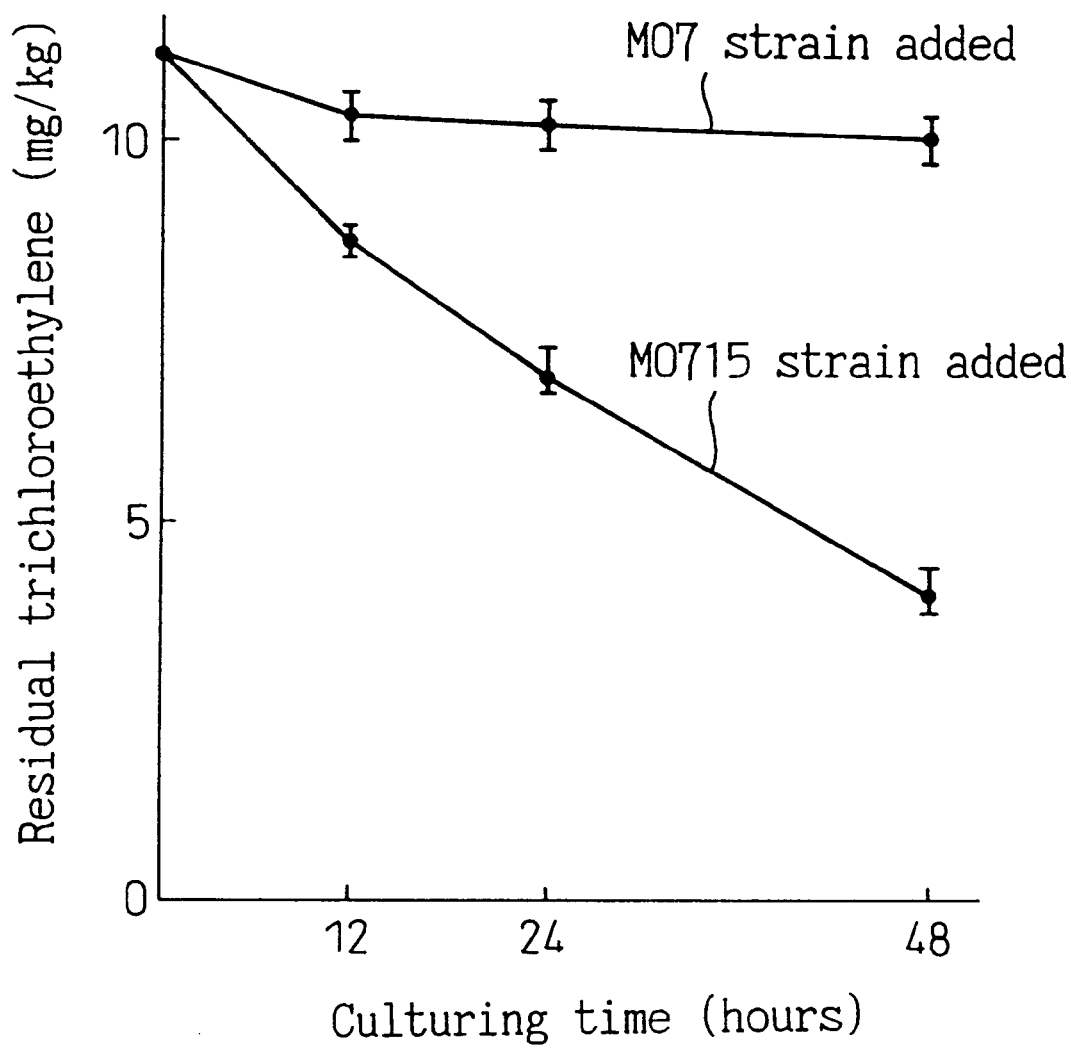
FIG. 26 is a graph which shows a result when trichloroethylene was decomposed by adding the cultured bacterial mass of strain MO7 of the present invention or strain MO715 which were grown on glutamic acid to the soil containing trichloroethylene.

The result as shown in FIG. 25 indicated that trichloroethylene in the soil similarly decreased from about 14 mg/kg to about 1 mg/kg in the NMS medium and the PH medium. Due to the addition of phenol into the soil, autochthonous microorganisms contributed to reduction of trichloroethylene, but the result indicated a greater effect came from the addition of strain MO7. Therefore, it is clear that the possibility can be ruled out that the strain exerts its effect not only in the sterilized culture medium but also in the natural environment although autochthonous microorganisms are present. It was confirmed that the activity of strain MO7 is sufficiently induced by adding phenol at an amount of about $10^6$ cells/g wet soil even in the natural environment.

Example 18. Construction of a Constitutive Mutant

A platinum loopful of the colony of the microorganism of the present invention which had been stored by passage on the agar plate containing 1.5% agar was picked and inoculated to a test tube containing 2 ml of the 1/3LB medium (its composition is shown in Table 11). After cultivating overnight under shaking at 30° C. at 130 r.p.m., an aliquot of the culture broth was diluted as appropriate, which was then plated to the plate of the 1/3LB medium containing 1.5% agar. After cultivating at 30° C. the number of cells was counted. The remainder of the culture broth was plated on a petri dish, which was then subjected to irradiation of a 15 W ultra violet lamp with a wavelength of 260 nm under the condition of a irradiation time of 3 minutes at a distance of 30 cm from the light source.

TABLE 10

| The 1/3 LB Medium | |
|---|---|
| Tryptone | 3.0 g |
| Yeast extract | 1.5 g |
| Sodium chloride | 3.0 g |
| Distilled water | 1.0 liter |

Then, the culture broth was diluted as appropriate and was plated to the plate of the 1/3LB medium containing 1.5% agar. After culturing at 30° C. the number of cells was counted to determine the death rate. When the death rate of 99% or higher was observed, it was assumed that there was enough mutation. From the culture broth at this point, the desired mutant were selected.

Catechol 2,3-dioxygenase (C23O) introduces oxygen into catechol to form 2-hydroxymuconic acid semialdehyde by metafission. This product is yellow-colored. When C23O is expressed after being sprayed, it readily turns yellow. The trichloroethylene degrading enzymes of the phenol-utilizing trichloroethylene-decomposing bacteria are known to be the phenol hydroxylase (PH) which convert phenol into catechol (M. Fujita et al., J. Ferment. Bioeng., 79: 100, 1995; V. Shingler et al., J. Bacteriol., 174: 711, 1992).

An example has been known that C23O is expressed by one operon in which the C23O gene is adjacent to the PH gene though C23O itself was not directly involved in the decomposition of trichloroethylene (M. Fujita et al., J. Ferment. Bioeng., 79: 100, 1995; V. Shingler et al., J. Bacteriol., 174: 711, 1992). If C23O is expressed in association with the PH, it is possible to select the strains which express the trichloroethylene-degrading enzyme using C23O expression as an indicator. The microorganism of the present invention, when cultivated using phenol as the only carbon source, decomposes phenol and the culture broth turns yellow with the growth of the bacterium. This will make said selection method applicable to the microorganism.

Accordingly, the suspension of the bacterial mass after mutation was diluted as appropriate and was plated to the plate of the 1/3LB medium containing 1.5% agar. After cultivating at 30° C. for 1 to 3 days, a catechol solution (0.1% (w/v) ethereal solution) was sprayed.

Then, when the death rate was 99.99%, about 10,000 colonies which appeared after ultra violet irradiation were investigated, which led to selection of 16 yellow colonies.

After the cononies were cultured in the 1/3LB liquid medium, it was plated to the plate of the 1/3LB medium containing 1.5% agar. After cultivating at 30° C., the colonies which appeared were sprayed with a catechol solution, and yellow colonies were isolated again to obtain the strains which consititutively express C23O.

A platinum loopful of these strains which consititutively express C23O were picked and inoculated into the M medium (its composition is shown in Table 12) containing 4 ml of sodium glutamate (0.1%) in a 20 ml vial. The vial was plugged with a butyl rubber septum and sealed with an aluminum cap, which was then cultivated at 30° C. under shaking for 2 days. Then trichloroethylene was added in an amount so that it became 30 ppm when all were dissolved in the liquid phase. After culturing at 30° C. for 5 days, trichloroethylene concentration was determined as in Example 6.

TABLE 11

| M medium | |
|---|---|
| Ammonium nitrate | 3.0 g |
| Disodium hydrogen phosphate | 2.2 g |
| Potassium dihydrogen phosphate | 0.8 g |
| Ferrous sulfate (II) heptahydrate | 10.0 mg |
| Calcium sulfate dihydrate | 10.0 mg |
| Magnesium sulfate heptahydrate | 10.0 mg |
| Yeast extracts | 50.0 mg |
| Distilled water | 1.0 liter, pH 7.0 |

The result demonstrated that the parent strain MO7 decomposed little trichloroethylene, but some of the strains which consititutively expressed C23O decomposed 52 to 34% of 30 ppm trichloroethylene. These microorganisms turned out to be a mutant which is derived from the parent strain MO7 and which can decompose trichloroethylene without requiring phenol.

Then, trichloroethylene decomposition in the soil is illustrated with reference to an example in which the strain MO715 which had the highest activity of decomposing trichloroethylene was used.

Example 19. Decomposition of Trichloroethylene by a Constitutive Mutant

A soil which was artificially contaminated with trichloroethylene (11 mg/kg soil) was prepared as in Example 9. After cultivating the strain MO715 under shaking at 30° C. for 2 days in 100 ml of the M medium containing sodium glutamate (0.1 w/v %), and then was centrifuged to harvest the cells, which were resuspended into an appropriate amount of the M medium so that the water content in the soil became 25%. After the suspension of the bacterial mass (containing no phenol) was added to the soil, the vial was sealed with a Teflon-coated rubber septum and was allowed to stand at 30° C. for a certain period of time. Trichloroethylene was analyzed in a method similar to that in Example 9. The culture broth cultivated on phenol and the strain MO7 were also analyzed in a similar manner.

As a result, after the addition of the suspension of the bacterial mass of the strain MO715 cultivated with sodium glutamate, about 35% of trichloroethylene was decomposed in 12 hours and about 60% in 48 hours. The strain MO7 grown on sodium glutamate decomposed little trichloroethylene. Thus, it was revealed that the microorganism of the present invention does not require phenol for induction and can decompose trichloroethylene in the soil as well.

From the foregoin it can be concluded that the present invention is an extremely safe technology since trichloroethylene can be decomposed without spreading toxic substances such as phenol into the environment.

Reference to the international deposition of microorganisms under the Budapest Treaty International Depository Authority: National Institute of Bioscience and Human-Technology Agency of Industrial Science and Technology Address: 1-3, Higashi 1-chome, Tsukuba-shi, Ibaraki, 305, Japan

| Identification | Deposition Number | Deposition Date |
|---|---|---|
| MO7 | FERM BP-5624 | Aug. 12, 1996 |
| MO715 | FERM BP-5928 | Apl. 24, 1997 |

What is claimed is:

1. An isolated bacterium which has the following properties:

| | |
|---|---|
| Morphology | coccoid, rod shaped |
| Gram staining | + |
| Spore forming | − |
| Motility | − |
| Relationship to oxygen | aerobic |
| Oxidase test | − |
| Catalase test | + |
| Resistance to acid | − |
| Rod-coccus cycle | + |
| Aerial mycelium formation | − |
| Peptide glycan type of cell wall | meso-diaminopimelic acid |
| Glycolyl test | − (acetyl type) |
| Mycolic acid | − |
| Major iseprenoid quinones | MK-8 (H4) |
| GC content of DNA (mole %) | 73 (by HPLC) | and, which can decompose trichloroethylene.

2. A bacterium according to claim 1 which is strain MO7 (FERM BP-5624).

3. A method for decomposing organic halogenated compounds and/or aromatic compounds, comprising subjecting said organic halogenated compounds and/or aromatic compounds to the action of a bacterium according to claim 1.

4. A method according to claim 3 wherein the organic halogenated compound is trichloroethylene and the aromatic compound is a phenolic compound.

5. A method for decomposing organic halogenated compounds in the soil, waste waters, or other waste products containing organic halogenated compounds, comprising adding a culture of a bacterium according to claim 1 to the soil, waste waters, or other waste products.

6. A method according to claim 5 wherein the organic halogenated compound is trichloroethylene and the culture is a cultured bacterial cells.

7. A method according to claim 5 wherein an aromatic compound is added to a culture medium for use in culturing to obtain the bacterial culture.

8. A method according to claim 7 wherein said aromatic compound is a phenolic compound.

9. A method according to claim 5 wherein an degradable carbon source is added to a culture medium for use in culturing to obtain the bacterial culture.

10. A method according to claim 9 wherein the degradable carbon source is glucose.

11. A method according to claim 5 wherein the culture is a cultured bacterial cells.

12. A method according to claim 11 wherein the cultured bacterial cells are living bacterial cells.

13. A method according to claim 11 wherein the cultured bacterial cells are sterilized cultured bacterial cells.

14. A method according to claim 13 wherein the sterilization treatment is ultraviolet irradiation.

15. A method for decomposing organic halogenated compounds in the soil, waste waters, or other waste products containing organic halogenated compounds, comprising the steps of inoculating a bacterium according to claim 1 to the soil, waste waters, or other waste products, adding an aromatic compound, an degradable carbon source, or a mixture thereof to the soil, waste waters, or other waste products, and then culturing said inoculated microorganism.

16. A method according to claim 15 wherein the organic halogenated compound is trichloroethylene.

17. A method according to claim 15 wherein the aromatic compound is a phenolic compound and the degradable carbon source is glucose.

18. A decomposition agent for organic halogenated compounds and/or aromatic compounds, comprising a bacterial culture according to claim 1.

19. A decomposition agent according to claim 18 wherein the culture is cultured bacterial cells.

20. A decomposition agent according to claim 19 wherein the culture is living bacterial cells.

21. A decomposition agent according to claim 19 wherein the cultured bacterial cells are sterilized bacterial cells.

22. A decomposition agent according to claim 21 wherein the sterilization treatment is ultraviolet irradiation.

23. A decomposition agent according to claim 18 which is in the form of dried bacterial cells.

24. A bacterium having the decomposition activity of organic halogenated compounds and/or aromatic compounds in the presence or absence of induction of an organic halogenated compound-decomposing enzyme by an aromatic compound, which bacterium is obtainable by subjecting a bacterium according to claim 1 to a mutation treatment and a selection procedure.

25. A bacterium according to claim 24 which is the strain MO715 (FERM BP-5928).

26. A method for decomposing organic halogenated compounds and/or aromatic compounds comprising allowing a bacterium according to claim 24 to act on the organic halogenated compounds and/or aromatic compounds.

27. A method according to claim 26 wherein the organic halogenated compound is trichloroethylene and the aromatic compound is a phenolic compound.

28. A method for decomposing organic halogenated compounds in the soil, waste waters, or other waste products containing organic halogenated compounds, comprising adding a culture of a bacterium according to claim 24 to the soil, waste waters, or other waste products.

29. A method according to claim 28 wherein the organic halogenated compound is trichloroethylene and the culture is cultured bacterial cells.

30. A method according to claim 28 wherein no aromatic compound is added to the culture medium for use in culturing to obtain said bacterial culture.

31. A method according to claim 28 wherein an degradable carbon source is added to the culture medium for use in culturing to obtain said bacterial culture.

32. A method according to claim 31 wherein the degradable carbon source is glutamic acid.

33. A method according to claim 28 wherein the culture is cultured bacterial cells.

34. A method according to claim 33 wherein the cultured bacterial cells are living bacterial cells.

35. A method according to claim 33 wherein the cultured bacterial cells are sterilized bacterial cells.

36. A method according to claim 35 wherein the sterilization treatment is ultraviolet irradiation.

37. A method for decomposing organic halogenated compounds in the soil, waste waters, or other waste products containing organic halogenated compounds, comprising the steps of inoculating a bacterium according to claim 24 to said soil, waste waters, or other waste products, adding an degradable carbon source to said soil, waste waters, or other waste products, and then culturing the inoculated microorganism.

38. A method according to claim 37 wherein the organic-halogenated compound is trichloroethylene.

39. A method according to claim 37 wherein the degradable carbon source is glutamic acid.

* * * * *

SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 1
gagtttgatc ctggctcag                                                     19

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 2
agaaaggagg tgatccagcc gcaggtt                                            27

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 3
ggccggacgg gtgagt                                                        16

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4
tacgggaggc agcag                                                         15

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
gtgccagcag ccgcgcg                                                       17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6

```
gattagatac cctggtag                                                      18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
actcaaagga attgacgg                                                      18

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 8
gcaacgagcg caaccc                                                        16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 9
tgtacacacc gcccgt                                                        16

<210> SEQ ID NO 10
<211> LENGTH: 1422
<212> TYPE: DNA
<213> ORGANISM: Unknown Sequence
<220> FEATURE:
<223> OTHER INFORMATION: Description of Unknown Sequence:
      Microorganism, strain M07
<223> OTHER INFORMATION: "n" bases may be a, t, c, g, other or unknown

<400> SEQUENCE: 10
aacgctggcg gcgtgcttaa cacatgcaag tcgaacggtg aagcttggag cttgcttcga        60
gtggatcagt ggcgaacggg tgagtaacac gtgagcaacc tgccccagac tctggaataa      120
gcgctggaaa cggcgtctaa tactggatat gtgacgyacc tgcatgggta ccgtctggaa      180 agttttttcgg tttgggatgg gctcgcggcc tatcagcttg ttggtgaggt aatggctcac     240
caaggcgaca acgggtancc ggcctgagag ggcgaccggc cacactggga ctgaaacacg      300
gcccaaactc ctacgggagg caccagtggg gaaatattgc acaatgggcg aaagcctgat      360
gcagcgacgc cgcgtgaggg atgacggcct tcgggttgta aacctctttc agcagggaag      420
aagcgaaagt gacggtacct gcagaataag caccggctaa ctacgtgcca gcagccgcgg      480
taatacgtag ggtgcgagcg ttgtccggaa ttattgggcg taaagagctt gtaggcggtt      540
tgtcgcgtct gctgtgaaaa tccggggctc aaccccggac ttgcagtggg tacgggcaga      600
ctagagtgtg gtaggggaga ctggaattcc tggtgtagcg gtgaaatgcg cagatatcag      660
gaggaacacc gatggcgaag gcaggtctct gggccactac tgacgctgag aagcgaaagc      720
atggggagcg aacaggatta gataccctgg tagtccatgc cgtaaacgtt gggcgctagg      780
```

-continued

```
tgtgggactc attccacgag ttccgtgccg cagctaacgc attaagcgcc ccgcctgggg      840
cagtacggcc gcaaggctaa aactcaaagg aattgacggg ggcccgcaca agcggcggag      900
catgcggatt aattcgatgc aacgcgaaga accttaccaa ggcttgacat ataccggaaa      960
cttccagaga tggttgcccc ctttgggtcg gtatacaggt ggtgcatggt tgtcgtcagc     1020
tcgtgtcgtg agatgttggg ttaagtcccg caacgagcgc aaccctcgtt ctatgttgcc     1080
agcacgtcat ggtggggact catggaagac tgccggggtc aactcggaag aaggtgggga     1140
tgacgtcaaa tcatcatgcc ccttatgtct tgggcttcac gcatgctaca atggccggta     1200
caaagggctg cgataccgca aggtggagcg aatccccaaa aaaccggtct cagttcggat     1260
tggggtctgc aactcgaccc catgaagtcg gagtcgctag taatcgcaaa tcagcaacgc     1320
tgcggtgaat actttcccgg gccttgtaca caccgcccgt caagtcacga aagttcggta     1380
acacccgaag ccggtggccc aaccttgtg gggggagccg tc                        1422
```